United States Patent
Esslinger et al.

(10) Patent No.: US 9,512,074 B2
(45) Date of Patent: *Dec. 6, 2016

(54) RADIOLABELED INHIBITORS OF THE AMINO ACID TRANSPORTERS ASCT1 AND ASCT2

(71) Applicant: The University of Montana, Missoula, MT (US)

(72) Inventors: Christopher Sean Esslinger, Missoula, MT (US); Michael P. Kavanaugh, Missoula, MT (US); Brent Lyda, Billings, MT (US); Nicholas R. Natale, Missoula, MT (US)

(73) Assignee: THE UNIVERSITY OF MONTANA, Missoula, MT (US)

( * ) Notice: Subject to any disclaimer, the term of this patent is extended or adjusted under 35 U.S.C. 154(b) by 91 days.

This patent is subject to a terminal disclaimer.

(21) Appl. No.: 14/515,103

(22) Filed: Oct. 15, 2014

(65) Prior Publication Data

US 2015/0056138 A1 Feb. 26, 2015

Related U.S. Application Data

(63) Continuation-in-part of application No. 13/549,779, filed on Jul. 16, 2012, now Pat. No. 8,895,607.

(60) Provisional application No. 61/508,512, filed on Jul. 15, 2011.

(51) Int. Cl.
| | |
|---|---|
| *A61K 51/04* | (2006.01) |
| *C07D 207/16* | (2006.01) |
| *C07B 59/00* | (2006.01) |

(52) U.S. Cl.
CPC ......... *C07D 207/16* (2013.01); *A61K 51/0446* (2013.01); *C07B 59/002* (2013.01)

(58) Field of Classification Search
CPC ............ C07D 207/16; A61K 51/0446; C07B 59/002
See application file for complete search history.

(56) References Cited

PUBLICATIONS

Antonia Sacchi et al (Journal of heterocyclic chemistry (1995) vol. 32 pp. 1067-1069).*

\* cited by examiner

*Primary Examiner* — Savitha Rao
*Assistant Examiner* — Angela Brown-Pettigrew
(74) *Attorney, Agent, or Firm* — Minerva, PLLC; Zachary Scott

(57) ABSTRACT

The present invention relates to a compound of Formula (I) or (II)

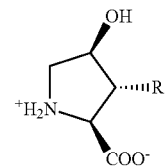

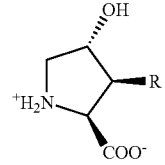

or a salt thereof, wherein R is described herein. The compounds are novel hydroxy-proline analog inhibitors of the ASCT1 and ASCT2 neutral amino acid transporters.

8 Claims, 5 Drawing Sheets

1

2

3

4

5

6

R = any group

CSE113

CSE125

CSE124

CSE127

CSE121

CSE112

CSE115

CSE132

CSE131

CSE122

CSE126

CSE130

RADIOLABELED INHIBITORS OF THE AMINO ACID TRANSPORTERS ASCT1 AND ASCT2

CROSS-REFERENCE TO RELATED APPLICATIONS

This application is a continuation-in-part of U.S. application Ser. No. 13/549,779, filed Jul. 16, 2012, which claims the benefit of the filing date of U.S. Provisional Patent Application Ser. No. 61/508,512, filed Jul. 15, 2011, the disclosures of which are incorporated by reference in their entirety.

STATEMENT REGARDING FEDERALLY SPONSORED RESEARCH OR DEVELOPMENT

This invention was made with government support under Grant No. R01 NS045704 awarded by the National Institute of Neurological Disorders and Grant No. R01 NS033270 awarded by the National Institutes of Health. The government has certain rights in this invention.

BACKGROUND OF THE INVENTION

The ASCT2 (SLC1A5) and ASCT1 (SLC1A4) transporters are transporters of neutral amino acids such as glutamine and a range of other neutral amino acids in and out of a cell in a $Na^+$ dependent, obligate amino acid exchange process. These transporters, by shuttling of various amino acids across the cell membrane, may facilitate or regulate various physiological processes such as cell growth, proliferation, or even glutamatergic neurotransmission via the glutamate/glutamine cycle.

ASCT2 inhibitors, such as L-γ-glutamyl-p-nitroanilide (GPNA) can be used as pharmacologic research tools to inhibit and investigate ASCT2-mediated amino acid transport and function. Such inhibitors can be used as chemotherapeutic agents alone or in combination with other chemotherapeutic agents to treat various human or mammalian tumors or cancers. These compounds can be used as antimetabolite agents alone or in combination with other chemotherapeutic agents to slow or prevent growth of various human or mammalian tumors and they can serve as effective anti-microbial agents to suppress growth of various pathogenic microbes. A need remains for additional inhibitors of ASCT transporters that can be used as pharmacologic tools to evaluate the physiologic significance of the ASCT transporter by pharmacologic intervention and thus better understand its role in various biologic pathways.

All patents, patent applications, provisional patent applications and publications referred to or cited herein are incorporated by reference in their entirety to the extent they are not inconsistent with the teachings of the specification.

BRIEF SUMMARY OF THE INVENTION

The present invention features novel trans-3-hydroxy-cis-4-benzyloxy-L-proline analogs that selectively and potently inhibit the neutral amino acid transporters ASCT2 (also known as SLC1A5) and ASCT1 (also known as SLC1A4). The compounds of the invention were screened by electrophysiological and radioligand uptake screening. The compounds of the invention can be used by neurophysiologists or molecular/cellular biologists to study the function and physiologic significance of the ASCT1 and ASCT2 transporters in a multitude of human and mammalian cells and tissues, including, e.g., tumor cell lines such as neuroblastomas, to study cell growth, proliferation, and glutamatergic neurotransmission via the glutamate/glutamine cycle. The compounds of the invention can further be used to treat patients (e.g., humans) suffering from diseases, conditions, disorders, or syndromes caused or influenced by abnormal ASCT1 or ASCT2 transporter dysfunction. Such diseases, conditions, disorders, and syndromes include, e.g., cancer, microbial infections, and ischemia-related central nervous system (CNS) injuries.

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them unless specified otherwise.

As used herein, the singular form "a," "an," and "the" include plural references unless the context clearly dictates otherwise. For example, the term "a cell" includes a plurality of cells, including mixtures thereof. The term "a nucleic acid molecule" includes a plurality of nucleic acid molecules.

The term "acyl," as used herein, alone or in combination, refers to a carbonyl attached to an alkenyl, alkyl, aryl, cycloalkyl, heteroaryl, heterocyclyl, or any other moiety where the atom attached to the carbonyl is carbon. An "acetyl" group refers to a —C(O)CH$_3$ group.

An "alkylcarbonyl" or "alkanoyl" group refers to an alkyl group attached to the parent molecular moiety through a carbonyl group. Examples of such groups include methylcarbonyl and ethylcarbonyl. Examples of acyl groups include formyl, alkanoyl and aroyl.

The term "alkenyl," as used herein, alone or in combination, refers to a straight-chain or branched-chain hydrocarbon radical having one or more double bonds optionally substituted and containing from 2 to 20, preferably 2 to 6, carbon atoms. Alkenylene refers to a carbon-carbon double bond system attached at two or more positions such as ethenylene [(—CH=CH—),(—C::C—)]. Examples of alkenyl radicals include ethenyl, propenyl, 2-methylpropenyl, 1,4-butadienyl and the like.

The term "alkoxy," as used herein, alone or in combination, refers to an alkyl ether radical, optionally substituted wherein the term alkyl is as defined below. Examples of alkyl ether radicals include methoxy, ethoxy, n-propoxy, isopropoxy, n-butoxy, iso-butoxy, sec-butoxy, tert-butoxy, and the like.

The term "alkyl," as used herein, alone or in combination, refers to a straight-chain or branched-chain alkyl radical optionally substituted containing from 1 to 20 and including 20, preferably 1 to 10, and more preferably 1 to 6, carbon atoms. Alkyl groups may be optionally substituted as defined herein. Examples of alkyl radicals include methyl, ethyl, n-propyl, isopropyl, n-butyl, isobutyl, sec-butyl, tert-butyl, pentyl, iso-amyl, hexyl, octyl, noyl and the like.

The term "alkylamino," as used herein, alone or in combination, refers to an alkyl group optionally substituted attached to the parent molecular moiety through an amino group. Alkylamino groups may be mono- or dialkylated, forming groups such as, for example, N-methylamino. N-ethylamino, N,N-dimethylamino, N,N-ethylmethylamino and the like.

The term "alkylthio," as used herein, alone or in combination, refers to an alkyl thioether (R—S—) radical wherein the term alkyl is as defined above and wherein the sulfur may be singly or doubly oxidized. Examples of alkyl thioether radicals include methylthio, ethylthio, n-propylthio, isopropylthio, n-butylthio, iso-butylthio, sec-butylthio, tert-butylthio, methanesulfonyl, ethanesulfinyl, and the like.

The term "alkynyl," as used herein, alone or in combination, refers to a straight-chain or branched chain hydrocarbon radical having one or more triple bonds and containing from 2 to 20, preferably from 2 to 6, more preferably from 2 to 4, carbon atoms. "Alkynylene" refers to a carbon-carbon triple bond attached at two positions such as ethynylene (—(C:::C—, —C≡C—). Examples of alkynyl radicals include ethynyl, propynyl, hydroxypropynyl, butyn-1-yl, butyn-2-yl, pentyn-1-yl, 3-methylbutyn-1-yl, hexyn-2-yl, and the like.

The terms "amido" and "carbamoyl," as used herein, alone or in combination, refer to an amino group as described below attached to the parent molecular moiety through a carbonyl group, or vice versa.

The term "amino," as used herein, alone or in combination, refers to —NRR', wherein R and R' are independently selected from the group consisting of hydrogen, alkyl, acyl, heteroalkyl, aryl, cycloalkyl, heteroaryl, and heterocycloalkyl, any of which may themselves be optionally substituted.

The term "aryl," as used herein, alone or in combination, means a carbocyclic aromatic system containing one, two or three rings wherein such rings may be attached together in a pendent manner or may be fused optionally substituted with at least one halogen, an alkyl containing from 1 to 3 carbon atoms, an alkoxyl, an aryl radical, a nitro function, a polyether radical, a heteroaryl radical, a benzoyl radical, an alkyl ester group, a carboxylic acid, a hydroxyl optionally protected with an acetyl or benzoyl group, or an amino function optionally protected with an acetyl or benzoyl group or optionally substituted with at least one alkyl containing from 1 to 12 carbon atoms.

The term "arylalkyl" or "aralkyl," as used herein, alone or in combination, refers to an aryl group attached to the parent molecular moiety through an alkyl group.

The term "aryloxy," as used herein, alone or in combination, refers to an aryl group attached to the parent molecular moiety through an oxygen atom.

The term "polyether radical" means a polyether radical containing from 2 to 6 carbon atoms interrupted with at least one oxygen atom, such as methoxymethyl, ethoxymethyl or methoxyethoxymethyl radicals or methoxyethyl.

The terms "benzo" and "benz," as used herein, alone or in combination, refer to the divalent radical $C_6H_4=$ derived from benzene. Examples include benzothiophene and benzimidazole.

The term "carbamate," as used herein, alone or in combination, refers to an ester of carbamic acid (—NHCOO—) which may be attached to the parent molecular moiety from either the nitrogen or acid end, and which may be optionally substituted as defined herein.

The term "carbonyl," as used herein, when alone includes formyl [—C(O)H] and in combination is a —C(O)— group.

The term "carboxy," as used herein, refers to —C(O)OH or the corresponding "carboxylate" anion, such as is in a carboxylic acid salt. An "O-carboxy" group refers to a RC(O)O— group, where R is as defined herein. A "C-carboxy" group refers to a —C(O)OR groups where R is as defined herein.

The term "cyano," as used herein, alone or in combination, refers to —CN.

The term "cycloalkyl," or, alternatively, "carbocycle," as used herein, alone or in combination, refers to a saturated or partially saturated monocyclic, bicyclic or tricyclic alkyl radical wherein each cyclic moiety contains from 3 to 12, preferably five to seven, carbon atom ring members and which may optionally be a benzo-fused ring system which is optionally substituted as defined herein. Examples of such cycloalkyl radicals include cyclopropyl, cyclobutyl, cyclopentyl, cyclohexyl, cycloheptyl, octahydronaphthyl, 2,3-dihydro-1H-indenyl, adamantyl and the like. "Bicyclic" and "tricyclic" as used herein are intended to include both fused ring systems, such as decahydonapthalene, octahydronapthalene as well as the multicyclic (multicentered) saturated or partially unsaturated type. The latter type of isomer is exemplified in general by, bicyclo[1,1,1]pentane, camphor, adamantane, and bicyclo[3,2,1]octane.

The term "ester," as used herein, alone or in combination, refers to a carboxy group bridging two moieties linked at carbon atoms.

The term "ether," as used herein, alone or in combination, refers to an oxygen atom bridging two moieties linked at carbon atoms.

The term "halo," or "halogen," as used herein, alone or in combination, refers to fluorine, chlorine, bromine, or iodine.

The term "haloalkyl," as used herein, alone or in combination, refers to an alkyl radical having the meaning as defined above wherein one or more hydrogens are replaced with a halogen. Specifically embraced are monohaloalkyl, dihaloalkyl and polyhaloalkyl radicals. A monohaloalkyl radical, for one example, may have an iodo, bromo, chloro or fluoro atom within the radical. Dihalo and polyhaloalkyl radicals may have two or more of the same halo atoms or a combination of different halo radicals. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Haloalkylene" refers to a haloalkyl group attached at two or more positions. Examples include fluoromethylene (—CFH—), difluoromethylene (—CF$_2$—), chloromethylene (—CHCl—) and the like.

The term "heteroalkyl," as used herein, alone or in combination, refers to a stable straight or branched chain, or cyclic hydrocarbon radical, or combinations thereof, fully saturated or containing from 1 to 3 degrees of unsaturation, consisting of the stated number of carbon atoms and from one to three heteroatoms selected from the group consisting of O, N, and S, and wherein the nitrogen and sulfur atoms may optionally be oxidized and the nitrogen heteroatom may optionally be quaternized. The heteroatom(s) O, N and S may be placed at any interior position of the heteroalkyl group. Up to two heteroatoms may be consecutive, such as, for example, —CH$_2$—NH—OCH$_3$.

The term "heteroaryl," as used herein, alone or in combination, refers to 3 to 7 membered, preferably 5 to 7 membered, unsaturated heteromonocyclic rings, or fused polycyclic rings in which at least one of the fused rings is unsaturated, wherein at least one atom is selected from the group consisting of O, S, and N. The term also embraces fused polycyclic groups wherein heterocyclic radicals are fused with aryl radicals, wherein heteroaryl radicals are fused with other heteroaryl radicals, or wherein heteroaryl radicals are fused with cycloalkyl radicals. Examples of heteroaryl groups include pyrrolyl, pyrrolinyl, imidazolyl, pyrazolyl, pyridyl, pyrimidinyl, pyrazinyl, pyridazinyl, triazolyl, pyranyl, furyl, thienyl, oxazolyl, isoxazolyl, oxadiazolyl, thiazolyl, thiadiazolyl, isothiazolyl, indolyl, isoindolyl, indolizinyl, benzimidazolyl, quinolyl, isoquinolyl, quinoxalinyl, quinazolinyl, indazolyl, benzotriazolyl, benzodioxolyl, benzopyranyl, benzoxazolyl, benzoxadiazolyl, benzothiazolyl, benzothiadiazolyl, benzofuryl, benzothienyl, chromonyl, coumarinyl, benzopyranyl, tetrahydroquinolinyl, tetrazolopyridazinyl, tetrahydroisoquinolinyl, thienopyridinyl, furopyridinyl, pyrrolopyridinyl and the like. Exemplary tricyclic heterocyclic groups include carbazolyl, benzidolyl, phenanthrolinyl, dibenzofuranyl, acridinyl, phenanthridinyl, xanthenyl and the like.

The terms "heterocycloalkyl" and, interchangeably, "heterocyclyl," as used herein, alone or in combination, each refer to a saturated, partially unsaturated, or fully unsaturated monocyclic, bicyclic, or tricyclic heterocyclic radical containing at least one, preferably 1 to 4, and more preferably 1 to 2 heteroatoms as ring members, wherein each said heteroatom may be independently selected from the group consisting of nitrogen, oxygen, and sulfur, and wherein there are preferably 3 to 8 ring members in each ring, more preferably 3 to 7 ring members in each ring, and most preferably 5 to 6 ring members in each ring. "Heterocycloalkyl" and "heterocyclyl" are intended to include sulfones, sulfoxides. N-oxides of tertiary nitrogen ring members, and carbocyclic fused and benzo fused ring systems; additionally, both terms also include systems where a heterocycle ring is fused to an aryl group, as defined herein, or an additional heterocycle group. Heterocyclyl groups of the invention are exemplified by aziridinyl, azetidinyl, 1,3-benzodioxolyl, dihydroisoindolyl, dihydroisoquinolinyl, dihydrocinnolinyl, dihydrobenzodioxinyl, dihydro[1,3]oxazolo[4,5-b]pyridinyl, benzothiazolyl, dihydroindolyl, dihydropyridinyl, 1,3-dioxanyl, 1,4-dioxanyl, 1,3-dioxolanyl, isoindolinyl, morpholinyl, piperazinyl, pyrrolidinyl, tetrahydropyridinyl, piperidinyl, thiomorpholinyl, and the like. The heterocyclyl groups may be optionally substituted unless specifically prohibited.

The term "hydroxy," as used herein, alone or in combination, refers to —OH.

The phrase "in the main chain" refers to the longest contiguous or adjacent chain of carbon atoms starting at the point of attachment of a group to the compounds of this invention.

The phrase "linear chain of atoms" refers to the longest straight chain of atoms independently selected from carbon, nitrogen, oxygen and sulfur.

The term "lower," as used herein, alone or in combination, means containing from 1 to and including 6 carbon atoms.

The term "nitro," as used herein, alone or in combination, refers to —NO$_2$.

The term "perhaloalkyl" as used herein, alone or in combination, refers to an alkyl group where all of the hydrogen atoms are replaced by halogen atoms.

Any definition herein may be used in combination with any other definition to describe a composite structural group. By convention, the trailing element of any such definition is that which attaches to the parent moiety. For example, the composite group alkylamido would represent an alkyl group attached to the parent molecule through an amido group, and the term alkoxyalkyl would represent an alkoxy group attached to the parent molecule through an alkyl group.

When a group is defined to be "null," what is meant is that said group is absent.

The term "optionally substituted" means the anteceding group may be substituted or unsubstituted. When substituted, the substituents of an "optionally substituted" group may include, without limitation, one or more substituents independently selected from the following groups or a particular designated set of groups, alone or in combination: lower alkyl, lower alkenyl, lower alkynyl, lower alkanoyl, lower heteroalkyl, lower heterocycloalkyl, lower haloalkyl, lower haloalkenyl, lower haloalkynyl, lower perhaloalkyl, lower perhaloalkoxy, lower cycloalkyl, phenyl, aryl, aryloxy, lower alkoxy, lower haloalkoxy, oxo, lower acyloxy, carbonyl, carboxyl, lower alkylcarbonyl, lower carboxyester, lower carboxamido, cyano, hydrogen, halogen, hydroxy, amino, lower alkylamino, arylamino, amido, nitro, thiol, lower alkylthio, arylthio, lower alkylsulfinyl, lower alkylsulfonyl, arylsulfinyl, arylsulfonyl, arylthio, sulfonate, sulfonic acid, trisubstituted silyl, N$_3$, SH, SCH$_3$, C(O)CH$_3$, CO$_2$CH$_3$, CO$_2$H, pyridinyl, thiophene, furanyl, lower carbamate, and lower urea. Two substituents may be joined together to form a fused five-, six-, or seven-membered carbocyclic or heterocyclic ring consisting of zero to three heteroatoms, for example forming methylenedioxy or ethylenedioxy. An optionally substituted group may be unsubstituted (e.g., —CH$_2$CH$_3$), fully substituted (e.g., —CF$_2$CF$_3$), monosubstituted (e.g., —CH$_2$CH$_2$F) or substituted at a level anywhere in-between fully substituted and monosubstituted (e.g., —CH$_2$CF$_3$). Where substituents are recited without qualification as to substitution, both substituted and unsubstituted forms are encompassed. Where a substituent is qualified as "substituted," the substituted form is specifically intended. Additionally, different sets of optional substituents to a particular moiety may be defined as needed; in these cases, the optional substitution will be as defined, often immediately following the phrase, "optionally substituted with."

Asymmetric centers exist in the compounds of the present invention. These centers are designated by the symbols "R" or "S," depending on the configuration of substituents around the chiral carbon atom. It should be understood that the invention encompasses all stereochemical isomeric forms, including diastereomeric, enantiomeric, and epimeric forms, as well as d-isomers and l-isomers, and mixtures thereof. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, direct separation of enantiomers on chiral chromatographic columns, or any other appropriate method known in the art. Starting compounds of particular stereochemistry are either commercially available or can be made and resolved by techniques known in the art. Additionally, the compounds of the present invention may exist as geometric isomers. The present invention includes all cis, trans, syn, anti, entgegen (E), and zusammen (Z) isomers as well as the appropriate mixtures thereof. Additionally, compounds may exist as tautomers; all tautomeric isomers are provided by this invention. Additionally, the compounds of the present invention can exist in unsolvated as well as solvated forms with pharmaceutically acceptable solvents such as water, ethanol, and the like. In general, the solvated forms are considered equivalent to the unsolvated forms for the purposes of the present invention.

Optical isomers are compounds with the same molecular formula but differ in the way they rotate plane polarized light. There are two types of optical isomers. The first type of optical isomers are compounds that are mirror images of one another but cannot be superimposed on each other. These isomers are called "enantiomers." The second type of optical isomers are molecules that are not mirror images but each molecule rotates plane polarized light and are considered optically-active. Such molecules are called "diastereoisomers." Diastereoisomers differ not only in the way they rotate plane polarized light, but also their physical properties. The term "optical isomer" comprises more particularly the enantiomers and the diastereoisomers, in pure form or in the form of a mixture.

The term "bond" refers to a covalent linkage between two atoms, or two moieties when the atoms joined by the bond are considered to be part of larger substructure. A bond may be single, double, or triple unless otherwise specified. A dashed line between two atoms in a drawing of a molecule indicates that an additional bond may be present or absent at that position.

The terms "cancer" refers to or describes the physiological condition in mammals that is typically characterized by unregulated cell growth. Examples of cancer include but are not limited to, carcinoma, lymphoma, blastoma, sarcoma, and leukemia. More particular examples of such cancers include squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma and various types of head and neck cancer.

The term "combination therapy" means the administration of two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients or in multiple, separate capsules for each active ingredient. In addition, such administration also encompasses use of each type of therapeutic agent in a sequential manner. In either case, the treatment regimen will provide beneficial effects of the drug combination in treating the conditions or disorders described herein. The term "imaging agent" as used herein refers to any moiety useful for the detection, tracing, or visualization of a compound of the invention when coupled thereto. Imaging agents include, e.g., an enzyme, a fluorescent label (e.g., fluorescein), a luminescent label, a bioluminescent label, a magnetic label, a metallic particle (e.g., a gold particle), a nanoparticle, an antibody or fragment thereof (e.g., a Fab, Fab', or $F(ab')_2$ molecule), and biotin. An imaging agent can be coupled to a compound of the invention by, for example, a covalent bond, ionic bond, van der Waals interaction or a hydrophobic bond. An imaging agent of the invention can be a radiolabel coupled to a compound of the invention, or a radioisotope incorporated into the chemical structure of a compound of the invention. Methods of detecting such imaging agents include, but are not limited to, positron emission tomography (PET), X-ray computed tomography (CT) and magnetic resonance imaging (MRI).

The phrase "therapeutically effective" is intended to qualify the amount of active ingredients used in the treatment of a disease or disorder. This amount will achieve the goal of reducing or eliminating the disease or disorder.

The term "therapeutically acceptable" refers to those compounds (or salts, esters, prodrugs, tautomers, zwitterionic forms, etc. thereof) which are suitable for use in contact with the tissues of patients without undue toxicity, irritation, and allergic response, are commensurate with a reasonable benefit/risk ratio, and are effective for their intended use.

As used herein, reference to "treatment" of a patient is intended to include prophylaxis. The term "patient" means all mammals including humans. Examples of patients include humans, cows, dogs, cats, goats, sheep, pigs, rabbits, and rodents (e.g., rats, mice, and guinea pigs).

The term "prodrug" refers to a compound that is made more active in vivo. Certain compounds of the present invention may also exist as prodrugs, as described in *Hydrolysis in Drug and Prodrug Metabolism: Chemistry, Biochemistry, and Enzymology*, Testa, Bernard and Wiley-VHCA, Zurich, Switzerland 2003. Prodrugs of the compounds described herein are structurally modified forms of the compound that readily undergo chemical changes under physiological conditions to provide the compound. Additionally, prodrugs can be converted to the compound by chemical or biochemical methods in an ex vivo environment. For example, prodrugs can be slowly converted to a compound when placed in a transdermal patch reservoir with a suitable enzyme or chemical reagent. Prodrugs are often useful because, in some situations, they may be easier to administer than the compound, or parent drug. They may, for instance, be bio-available by oral administration whereas the parent drug is not. The prodrug may also have improved solubility in pharmaceutical compositions over the parent drug. A wide variety of prodrug derivatives are known in the art, such as those that rely on hydrolytic cleavage or oxidative activation of the prodrug. An example, without limitation, of a prodrug is a compound which is administered as an ester (the "prodrug"), but then is metabolically hydrolyzed to the carboxylic acid, the active entity. Additional examples include peptidyl derivatives of a compound.

The compounds of the invention can exist as therapeutically acceptable salts. The present invention includes compounds listed above in the form of salts, in particular acid addition salts. Suitable salts include those formed with both organic and inorganic acids. Such acid addition salts will normally be pharmaceutically acceptable. However, salts of non-pharmaceutically acceptable salts may be of utility in the preparation and purification of the compound in question. Basic addition salts may also be formed and be pharmaceutically acceptable. For a more complete discussion of the preparation and selection of salts, refer to Stahl, P. Heinrich. *Pharmaceutical Salts: Properties, Selection, and Use*, Wiley-VCHA, Zurich, Switzerland (2002).

The term "therapeutically acceptable salt," as used herein, represents salts or zwitterionic forms of the compounds of the present invention which are water or oil-soluble or dispersible and therapeutically acceptable as defined herein. The salts can be prepared during the final isolation and purification of the compounds or separately by reacting the appropriate compound in the form of the free base with a suitable acid. Representative acid addition salts include acetate, adipate, alginate, L-ascorbate, aspartate, benzoate, benzenesulfonate (besylate), bisulfate, butyrate, camphorate, camphorsulfonate, citrate, digluconate, formate, fumarate, gentisate, glutarate, glycerophosphate, glycolate, hemisulfate, heptanoate, hexanoate, hippurate, hydrochloride, hydrobromide, hydroiodide, 2-hydroxyethansulfonate (isethionate), lactate, maleate, malonate, DL-mandelate, mesitylenesulfonate, methanesulfonate, naphthylenesulfonate, nicotinate, 2-naphthalenesulfonate, oxalate, pamoate, pectinate, persulfate, 3-phenylproprionate, phosphonate, picrate, pivalate, propionate, pyroglutamate, succinate, sulfonate, tartrate, L-tartrate, trichloroacetate, trifluoroacetate, phosphate, glutamate, bicarbonate, para-toluenesulfonate (p-tosylate), and undecanoate. Also, basic groups in the compounds of the present invention can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form therapeutically acceptable addition salts include inorganic acids such as hydrochloric, hydrobromic, sulfuric, and phosphoric, and organic acids such as oxalic, maleic, succinic, and citric. Salts can also be formed by coordination of the compounds with an alkali metal or alkaline earth ion. Hence, the present invention contemplates sodium, potassium, magnesium, and calcium salts of the compounds of the compounds of the present invention and the like.

DETAILED DESCRIPTION OF THE INVENTION

Figure 1:
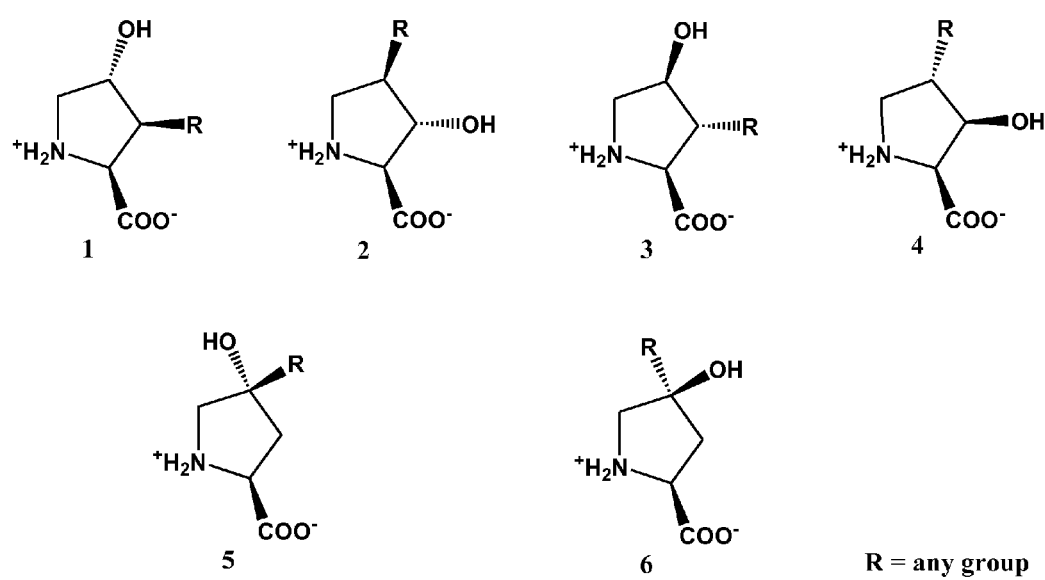
FIG. 1 shows the chemical structures of exemplary substituted prolinol compounds of the invention.

The present invention features alkyl, alkyl-ether, aryl and aryl-ether substituted hydroxy-L-proline derivative compounds that are useful as pharmacologic inhibitors of the amino acid transporters ASCT2 (gene SLC1A5) and ASCT1 (gene SLC1A4). The compounds of the invention can be used, without limitation, to inhibit ASCT2 or ASCT 1 as cancer chemotherapeutic agents (e.g., to treat a patient (e.g., a human)), as neuroprotective agents in ischemia-related central nervous system (CNS) injuries, as inhibitors of microbial growth or infection, and as pharmacological tools to investigate ASCT1 or ASCT2 physiological functions (e.g., in clinical or research settings). Furthermore, the compounds of the invention are useful for in diagnostic imaging applications, such as the imaging of ASCT 1 and ASCT2 by radiography, such as positron emission tomography (PET).

Compounds of the Invention

The compounds of the invention are represented by formulae A-D:

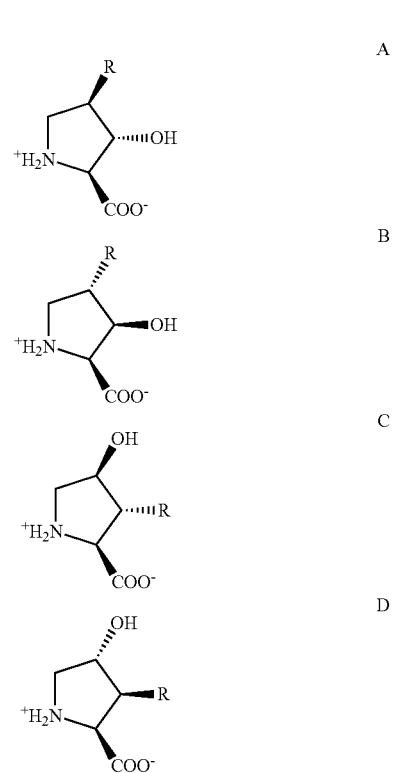

or a salt, ester or prodrug thereof, wherein R is selected from the group consisting of alkyl, alkyl-ether, aryl, and aryl-ether. The compounds of the invention can be prepared in combination with a pharmaceutically acceptable excipient.

The invention further features compounds and methods useful for in vivo or in vitro radiographic imaging studies of ASCT1/ASCT2 activity or expression in a patient (e.g., a human) or a sample derived therefrom (e.g., a biopsy). The discovery of these compounds and related processes represent an unexpected advance in the art of radiotracer chemistry as fluorine-18 complexes are notoriously difficult to synthesize (Lee et al., A Fluoride-Derived Electrophilic Late-State Fluorination Reagent for PET Imaging, *Science* 334:639 (2011), hereby incorporated by reference). The addition of such a radionuclide tag (e.g., fluorine-18) to the genus of ASCT1 and ASCT2 inhibitors described above yields a "diagnostic" compound that can be imaged using, e.g., a PET scanner. Diagnostic imaging studies using these diagnostic compounds of the invention can be performed in vivo or in patient biopsies and tissue samples ex vivo. Similarly, the diagnostic compounds of the invention are also useful for the in vitro or ex vivo study of ASCT1 and ASCT2 activity and disease processes for biomedical research purposes.

The invention also features methods of synthesizing the compounds of the invention described herein, as well as methods of treating a patient (e.g., a human) suffering from, or at risk of developing, a condition characterized by or related to ASCT1 or ASCT2, including but not limited to cancer, ischemia-related central nervous system (CNS) injuries, and microbial infections.

Methods of Treatment

The compounds of the invention can be used to treat a patient (e.g., a human) that suffers from or is at risk of suffering from a disease, disorder, condition, or symptom caused by or related to ASCT1 or ASCT2 functional abnormality, including, but not limited to, cancer and ischemia-related central nervous system injuries. The compounds of the invention can be used alone or in combination with other agents and compounds to treat such diseases, disorders, conditions, and symptoms. Each such treatment described herein includes the step of administering to a patient in need thereof a therapeutically effective amount of a compound of the invention described herein to delay, reduce or prevent such disease, disorder, condition, or symptom.

Cancer

Research has revealed that ASCT1/ASCT2 play a role in several disease processes, including cancer and ischemia-related central nervous system injuries. Accordingly, inhibition of ASCT1/ASCT2 has been shown effective to prevent or treat these disease processes. For example, targeting the ASCT2 transporter has been identified as a therapy to inhibit cancer cells (reviewed in: Nakanishi et al., *J. Pharm. Sci.* 100:3731 (2011)). Antisense mRNA to specifically down-regulate ASCT2 effectively inhibits survival of human hepatoma cells (Fuchs et al., *Am. J. Physiol. Cell. Physiol.* 293 C55 (2007)).

The involvement of ASCT1/ASCT2 glutamine transport abnormality or dysfunction is involved in a broad spectrum of cancer types and subtypes. For example, glutamine metabolism and glutamine transport by the ASCT2 transporter is up-regulated in a wide variety of tumor cell types, which gives them a growth advantage over normal cells (Fuchs et al., *Sem. Cancer Biol.*, 15:254-266 (2005)). Specifically, ASCT2 was upregulated (statistically significant) in brain, colon, eye, kidney, liver, lung, lymph node, mammary gland, muscle, pancreas, placenta, skin, and stomach. Other studies show the broad expression and dependence of various cancer cells on the obligate glutamine transporters ASCT1/ASCT2, such as in breast cancer (Collins et al., *J. Cell Physiol.*, 176:166-178 (1998)) and colon carcinoma (Wasa et al., *Ann. Surg.*, 22:189-97 (1996)).

Ischemia-Related Central Nervous System Injury

ASCT1/ASCT2 glutamine transport abnormalities also play a role in ischemia-related central nervous system injuries. For example, Wolosker et al. (FEBS Journal, 275:3514-3526 (2008)) describes the role that glutamate transporters (such as ASCT1/2) play in the regulation of NMDAR receptors. NMDAR receptor activity has been correlated with neuronal damage following ischemia (i.e., stroke). One way to control NMDAR activity is to limit the availability of its agonist ligand, D-serine. Glutamate ASCT1/2 inhibition, as provided by the compounds and methods of the present invention, limits the level of D-serine available to NMDAR receptors, thereby limiting NMDAR activity and conferring a neuroprotective benefit.

Besides being useful for human treatment, the compounds and formulations of the present invention are also useful for the treatment of ASCT1 and ASCT2 functional abnormality in animals, e.g., the veterinary treatment of domesticated animal, companion animals (e.g., dogs and cats), exotic animals, farm animals (e.g., ungulates, including horses, cows, sheep, goats, and pigs), and animals used in scientific research (e.g., rodents).

Methods of Diagnostic Imaging

Compounds of the invention that contain a radionuclide, such as fluorine-18, can also be used, alone or in combination with other agents and compounds, in radiographic medical imaging applications in a patient (e.g., a human) to diagnose or follow the progression of diseases, disorders, conditions or symptoms related to a disease, disorder, condition, or symptom caused by or related to ASCT1 or ASCT2 functional abnormality, including, but not limited to, cancer, microbial infections, and ischemia-related central nervous system injuries. Radiologists and other medical clinicians are skilled in the use of radiographic imaging devices, such as positron emission tomography (PET) scanners, and methods of imaging diagnostic compounds, such as the radionuclide compounds of the invention, in a patient are widely known (e.g., Saha, Basics of PET Imaging: Physics, Chemistry, and Regulations, Springer (2010) ISBN 978-1-4419-0804-9, hereby incorporated by reference).

The radionuclide compounds and formulations of the present invention are also useful for the medical imaging of animals, e.g., the veterinary treatment of domesticated animal, companion animals (e.g., dogs and cats), exotic animals, farm animals (e.g., ungulates, including horses, cows, sheep, goats, and pigs), and animals used in scientific research (e.g., rodents and non-human primates).

Methods of Radionuclide Compound Synthesis

The radionuclide diagnostic compounds of the invention can be synthesized by several techniques known to persons skilled in the art. For example, for the substitution of a carbon atom by a carbon-11, several derivatives such as [$^{11}$C]methyl iodide or [$^{11}$C]methyl triflate (Welch et al., In Handbook of Radiopharmaceuticals-Radiochemistry and Applications (Welch M J, Redvanly C S Eds.), New York-Chichester-Brisbane-Toronto, Wiley-Interscience Pub., 1-848 (2003)).

In the case of a labeling with fluorine-18, the radioisotope may be directly attached to a core structure by nucleophilic aliphatic or aromatic (including heteroaromatic (Dollé et al., *Curr. Pharm. Design* 11:3221-3235 (2005)) substitutions or electrophilic substitutions or linked through the addition of a spacer group, both techniques known to persons skilled in the art (Kilbourn, In fluorine-18 Labeling of Radiopharmaceuticals, Nuclear Science Series (Kilbourn M R Ed.), National Academy Press, Washington, D.C., 1-149 (1990); Lasne et al., *Topics in Current Chemistry* 222:201-258 (2002); Cai et al., *Eur. J. Org. Chem.* 17:2853-2873 (2008); and Dollé et al., In Fluorine and Health: Molecular Imaging, Biomedical Materials and Pharmaceuticals, Tressaud A, Haufe G (Eds). Elsevier 3-65 (2008)). An alkyl, alkenyl or alkynyl linker may also be used for the addition of the fluorine-18 atom (Damont et al., *J. Label. Compds Radiopharm.* 51:286-292 (2008); Dollé et al., *Bioorg. Med. Chem.* 14:1115-1125 (2006); and Dollé et al., *J. Label. Compds Radiopharm.* 50:716-723 (2007)). Additional methods of producing radionuclide (e.g., fluorine-18) labeled compounds are described in U.S. Patent Application Publications No. 2006/0100465, 2010/0292478, and 2011/0184159, each hereby incorporated by reference.

In the case of a labeling with other halogens (e.g., bromine-76, iodine-123 or iodine-124), the radioisotope may also be directly attached by nucleophilic or electrophilic substitutions to a core structure or linked through the addition of a spacer group, both techniques known to persons skilled in the art (Maziere et al., *Curr. Pharm. Des.* 7:1931-1943 (2001); and Coenen et al., In Radioiodination reactions for pharmaceuticals-Compendium for effective synthesis strategies, Coenen H. H., Mertens J., Maziere B. (Eds), Springer Verlag, Berlin-Heidelberg, 1-101 (2006)).

In the case of the labeling with metal radioisotopes (e.g., gallium-68, copper-64 or technetium-99m), the preferred approach used, which will be considered by a person skilled in the art, is the use of a bifunctional chelating agent based on, for example, the open-chain polyaminocarboxylates ethylenediamine tetraacetic acid (EDTA) and diethylenetriamine pentaacetic acid (DTPA), the polyaminocarboxylic macrocycle 1,4,7,10-tetraazacyclododecane-1,4,7,10-tetraacetic acid (DOTA), mercaptoacetyldi- and triglycine (MAG2, MAG3), bis-(S-benzoyl-thioglycoloyl)diaminopropanoate ((SBT)$_2$DAP) and hydrazinonicotinic acid (HYNIC), facilitating the complexation of the radiometal cation at one function and the covalent attachment to a core molecule at another (Brunner et al., (1995) Radiotracer production—Radiometals and their chelates In Principle of Nuclear Medecine, Wagner H. N. (Ed). Saunders: Philadelphia, 220-228 (1995); Weiner R. E. et al., Chemistry of gallium and indium radiopharmaceuticals In Handbook of Radiopharmaceuticals-Radiochemistry and Applications (Welch M J, Redvanly C S Eds.), New York-Chichester-Brisbane-Toronto, Wiley-Interscience Pub., 363-400 (2003); Anderson et al., Chemistry of copper radionucleides and radiopharmaceutical products In Handbook of Radiopharmaceuticals—Radiochemistry and Applications (Welch M J, Redvanly C S Eds.), New York-Chichester-Brisbane-Toronto, Wiley-Interscience Pub., 401-422 (2003); and Mahmood et al., Technetium radiopharmaceuticals In Handbook of Radiopharmaceuticals—Radiochemistry and Applications (Welch M J, Redvanly C S Eds.), New York-Chichester-Brisbane-Toronto, Wiley-Interscience Pub., 323-362 (2003)).

Further methods of synthesizing the compounds of the invention are described below in the Examples.

The diagnostic compounds of the invention described herein that include a radionuclide (e.g., fluorine-18) can be synthesized to adjust the specific activity of the compound. Specific activity is defined as the radioactivity per unit mass of a radionuclide or a labeled compound. For example, if a 50 mg sample contains 100 mCi (370 MBq), then the specific activity of the sample is given as 100/50=2 mCi/mg or 74 MBq/mg. Specific activity should not be confused with the concentration of a compound containing a radionuclide, which are generally expressed in mCi/mL or MBq/mL. The specific activity is an important parameter to consider in radiolabeling and in vivo biodistribution of tracers, such as the radionuclide compounds of the invention. Cold molecules in low specific activity radiopharmaceuticals compete with radioactive molecules and lower the uptake of the tracer in the target tissue(s). Similarly, low specific activity radionuclides yield poor radiolabeling, and hence, poor radiography (e.g., PET). For these reasons, the diagnostic compounds of the invention containing fluorine-18 are synthesized having a specific activity of at least 1.0, 1.2, 1.4, 1.8, 2.0, 2.2, 2.4, or 2.6 Ci/mmol. In one embodiment of the invention, the fluorine-18 diagnostic compound has a specific activity of at least 1.0 Ci/mmol.

Persons having skill in the art are aware of methods that can increase or decrease the specific activity of a desired radionuclide compound of the invention. For example, electrophilic fluorination of palladium aryl complexes can be used to yield diagnostic compounds of the invention containing fluorine-18 with high specific activity (Lee et al., (2011)).

Compound Administration and Formulation

Basic addition salts can be prepared during the final isolation and purification of the compounds by reaction of a carboxy group with a suitable base such as the hydroxide, carbonate, or bicarbonate of a metal cation or with ammonia or an organic primary, secondary, or tertiary amine. The cations of therapeutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N'-dibenzylethylenediamine. Other representative organic amines useful for the formation of base addition salts include ethylenediamine, ethanolamine, diethanolamine, piperidine, and piperazine.

A salt of a compound can be made by reacting the appropriate compound in the form of the free base with the appropriate acid. The novel compounds described herein can be prepared in a form of pharmaceutically acceptable salts that will be prepared from nontoxic inorganic or organic bases including but not limited to aluminum, ammonium, calcium, copper, ferric, ferrous, lithium, magnesium, manganic salts, manganous, potassium, sodium, zinc, and the like. Salts derived from pharmaceutically acceptable organic non-toxic bases include salts of primary, secondary, and tertiary amines, substituted amines including naturally-occurring substituted amines, cyclic amines, and basic ion exchange resins, such as arginine, betaine, caffeine, choline, ethylamine, 2-diethylaminoethano, 1,2-dimethylaminoethanol, ethanolarnine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, trishydroxylmethyl amino methane, tripropyl amine, and tromethamine.

If the compounds of the invention are basic, salts could be prepared in a form of pharmaceutically acceptable salts that will be prepared from nontoxic inorganic or organic acids including but not limited to hydrochloric, hydrobromic, phosphoric, sulfuric, tartaric, citric, acetic, fumaric, alkylsulphonic, naphthalenesulphonic, para-toluenesulphonic, camphoric acids, benzenesulfonic, benzoic, camphorsulfonic, citric, ethanesulfonic, gluconic, glutamic, isethonic, lactic, maleic, malic, mandelic, methanesulfonic, mucic, nitric, pamoic, pantothenic, phosphoric, and succinic.

While it may be possible for the compounds of the invention to be administered as the raw chemical, it is also possible to present them as a pharmaceutical formulation. Accordingly, the present invention provides a pharmaceutical formulation comprising a compound or a pharmaceutically acceptable salt, ester, prodrug or solvate thereof, together with one or more pharmaceutically acceptable carriers thereof and optionally one or more other therapeutic ingredients. The carrier(s) must be "acceptable" in the sense of being compatible with the other ingredients of the formulation and not deleterious to the recipient thereof. Proper formulation is dependent upon the route of administration chosen. Any of the well-known techniques, carriers, and excipients may be used as suitable and as understood in the art; e.g., in Remington's Pharmaceutical Sciences. The pharmaceutical compositions of the present invention may be manufactured in a manner that is itself known, e.g., by means of conventional mixing, dissolving, granulating, dragee-making, levigating, emulsifying, encapsulating, entrapping or compression processes.

The formulations include those suitable for oral, parenteral (including subcutaneous, intradermal, intramuscular, intravenous, intraarticular, and intramedullary), intraperitoneal, transmucosal, transdermal, rectal and topical (including dermal, buccal, sublingual and intraocular) administration although the most suitable route may depend upon for example the condition and disorder of the recipient. The formulations may conveniently be presented in unit dosage form and may be prepared by any of the methods well known in the art of pharmacy. All methods include the step of bringing into association a compound of the present invention or a pharmaceutically acceptable salt, ester, prodrug or solvate thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

Pharmaceutical preparations which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. The tablets may optionally be coated or scored and may be formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

The compounds of the invention may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The formulations may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Formulations for parenteral administration include aqueous and non-aqueous (oily) sterile injection solutions of the active compounds which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

In addition to the formulations described previously, the compounds of the invention may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example, as an emulsion in an acceptable oil) or ion exchange resins, or as sparingly soluble derivatives, for example, as a sparingly soluble salt.

For buccal or sublingual administration, the compounds of the invention may take the form of tablets, lozenges, pastilles, or gels formulated in conventional manner. Such compositions may comprise the active ingredient in a flavored basis such as sucrose and acacia or tragacanth.

The compounds of the invention may also be formulated in rectal compositions such as suppositories or retention enemas, e.g., containing conventional suppository bases such as cocoa butter, polyethylene glycol, or other glycerides.

Compounds of the invention may be administered topically, that is by non-systemic administration. This includes the application of a compound of the present invention externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Formulations suitable for topical administration include solid, liquid or semi-liquid preparations suitable for penetration through the skin to the site of inflammation such as gels, liniments, lotions, creams, ointments or pastes, and drops suitable for administration to the eye, ear or nose. The active ingredient may comprise, for topical administration, from 0.001% to 10% w/w, for instance from 1% to 2% by weight of the formulation. It may however comprise as much as 10% w/w but preferably will comprise less than 5% w/w, more preferably from 0.1% to 1% w/w of the formulation.

Via the topical route, the pharmaceutical composition according to the invention may be in the form of liquid or semi liquid such as ointments, or in the form of solid such as powders. It may also be in the form of suspensions such as polymeric microspheres, or polymer patches and hydrogels allowing a controlled release. This topical composition may be in anhydrous form, in aqueous form or in the form of an emulsion. The compounds are used topically at a concentration generally of between 0.001% and 10% by weight and preferably between 0.01% and 1% by weight, relative to the total weight of the composition.

The compounds of the invention presented herein may also find an application in cosmetics, in particular in body and hair hygiene and more particularly for regulating and/or restoring skin lipid metabolism.

Cosmetic use of a composition comprising, in a physiologically acceptable support, at least one of the compounds described herein for body or hair hygiene are presented. The cosmetic composition, in a cosmetically acceptable support, at least one compound and/or an optical or geometrical isomer thereof or a salt thereof, and may be in the form of liquid or semi liquid such as ointments, creams or in the form of solid such as powders. It may also be in the form of suspensions such as polymeric microspheres or polymer patches and hydrogels allowing a controlled release. This topical composition may be in anhydrous form, in aqueous form or in the form of an emulsion. The concentration of compound in the cosmetic composition is between 0.001% and 5% by weight relative to the total weight of the composition. Finally, the present invention provides a cosmetic process for enhancing the skin, which consists in applying to the skin a composition comprising at least one compound presented herein.

For administration by inhalation, the compounds according to the invention are conveniently delivered from an insufflator, nebulizer pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, the compounds according to the invention may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhaler or insufflator.

Preferred unit dosage formulations are those containing an effective dose, as herein below recited, or an appropriate fraction thereof, of the active ingredient.

It should be understood that in addition to the ingredients particularly mentioned above, the formulations of this invention may include other agents conventional in the art having regard to the type of formulation in question, for example those suitable for oral administration may include flavoring agents.

Compounds according to the invention can be administered at a daily dose of about 0.001 mg/kg to 100 mg/kg of body weight, in 1 to 3 dosage intakes. Further, compounds can be used systemically, at a concentration generally of between 0.001% and 10% by weight and preferably between 0.01% and 1% by weight, relative to the weight of the composition.

The amount of active ingredient that may be combined with the carrier materials to produce a single dosage form will vary depending upon the host treated and the particular mode of administration.

The compounds of the invention can be administered in various modes, e.g. orally, topically, or by injection. The precise amount of compound administered to a patient will be the responsibility of the attendant physician. The specific dose level for any particular patient will depend upon a variety of factors including the activity of the specific compound employed, the age, body weight, general health, sex, diets, time of administration, route of administration, rate of excretion, drug combination, the precise disorder being treated, and the severity of the indication or condition being treated. Also, the route of administration may vary depending on the condition and its severity.

In certain instances, it may be appropriate to administer at least one of the compounds of the invention described herein (or a pharmaceutically acceptable salt, ester, or prodrug thereof) in combination with another therapeutic agent. By way of example only, if one of the side effects experienced by a patient upon receiving one of the compounds herein is hypertension, then it may be appropriate to administer an anti-hypertensive agent in combination with the initial therapeutic agent. Or, by way of example only, the therapeutic effectiveness of one of the compounds described herein may be enhanced by administration of an adjuvant (i.e., by itself the adjuvant may only have minimal therapeutic benefit, but in combination with another therapeutic agent, the overall therapeutic benefit to the patient is enhanced). Or, by way of example only, the benefit experienced by a patient may be increased by administering one of the compounds described herein with another therapeutic agent (which also includes a therapeutic regimen) that also has therapeutic benefit. By way of example only, in a treatment for pain involving administration of one of the compounds described herein, increased therapeutic benefit may result by also providing the patient with another therapeutic agent for pain. In any case, regardless of the disease, disorder or condition being treated, the overall benefit experienced by the patient may simply be additive of the two therapeutic agents or the patient may experience a synergistic benefit.

Specific, non-limiting examples of possible combination therapies include use of the compounds of the invention together with inert or active compounds, or other drugs including wetting agents, flavor enhancers, preserving agents, stabilizers, humidity regulators, pH regulators, osmotic pressure modifiers, emulsifiers, UV-A and UV-B screening agents, antioxidants, depigmenting agents such as hydroquinone or kojic acid, emollients, moisturizers, for instance glycerol, PEG 400, or urea, antiseborrhoeic or antiacne agents, such as S-carboxymethylcysteine, S-benzylcysteamine, salts thereof or derivatives thereof, or benzoyl peroxide, antibiotics, for instance erythromycin and tetracyclines, chemotherapeutic agent, for example, paclitaxel, antifungal agents such as ketoconazole, agents for promoting regrowth of the hair, for example, minoxidil (2,4-diamino-6-piperidinopyrimidine 3-oxide), non-steroidal anti-inflammatory agents, carotenoids, and especially p-carotene, antipsoriatic agents such as anthralin and its derivatives, eicosa-5,8,11,14-tetraynoic acid and eicosa-5,8,11-triynoic acid, and esters and amides thereof, retinoids, i.e. RAR or RXR receptor ligands, which may be natural or synthetic, corticosteroids or oestrogens, alpha-hydroxy acids and a-keto acids or derivatives thereof, such as lactic acid, malic acid, citric acid, and also the salts, amides or esters thereof, or p-hydroxy acids or derivatives thereof, such as salicylic acid and the salts, amides or esters thereof, ion-channel blockers such as potassium-channel blockers, or alternatively, more particularly for the pharmaceutical compositions, in combination with medicaments known to interfere with the immune system, anticonvulsant agents include, and are not limited to, topiramate, analogs of topiramate, carbamazepine, valproic acid, lamotrigine, gabapentin, phenytoin and the like and mixtures or pharmaceutically acceptable salts thereof. A person skilled in the art will take care to select the other compound(s) to be added to these compositions such that the advantageous properties intrinsically associated with the compounds of the invention are not, or are not substantially, adversely affected by the envisaged addition.

In any case, the multiple therapeutic agents (at least one of which is a compound of the present invention) may be administered in any order or even simultaneously. If simultaneously, the multiple therapeutic agents may be provided in a single, unified form, or in multiple forms (by way of example only, either as a single pill or as two separate pills). One of the therapeutic agents may be given in multiple doses, or both may be given as multiple doses. If not simultaneous, the timing between the multiple doses may be any duration of time ranging from a few minutes to four weeks.

Thus, in another aspect, methods for treating diseases, disorders, conditions, or symptoms in a patient (e.g., a human or animal patient) in need of such treatment are presented herein, the methods comprising the step of administering to the patient an amount of a compound of the invention effective to reduce or prevent the disease, disorder, condition, or symptom, in combination with at least one additional agent for the treatment of said disorder that is known in the art.

In a related aspect, therapeutic compositions having at least one novel compound of the invention described herein can be administered in combination with one or more additional agents for the treatment of any of the diseases, disorders, conditions, or symptoms described herein.

EXAMPLES

It is understood that the foregoing examples are merely illustrative of the present invention. Certain modifications of the articles and/or methods employed may be made and still achieve the objectives of the invention. Such modifications are contemplated as within the scope of the claimed invention.

Example 1

Procedure for Synthesis of N-Cbz-(trans or cis)-3,4-epoxy-L-proline benzyl ester To arrive at prolinol targets 1-4 (FIG. 1), trans-4-hydroxy-L-proline was converted to the protected trans- and cis-3,4-epoxides 13a & 13b as outlined in Scheme 1 or alternatively through elimination of a methyl-xanthate and epoxidation by mCPBA (Scheme 2).

Briefly, the amine of trans-4-hydroxy-L-proline was protected using benzylchloroformate in water at a pH approximately 10. The acid functionality of N-Cbz-trans-4-hydroxy-L-proline was then protected using benzylbromide, $Na_2CO_3$, NaI, in DMF at room temperature (approximately 22° C.) and isolated by silica chromatography. Compound 9 (Scheme 1) was then converted to the 4-tosylate using p-toluenesulphonyl chloride in pyridine at 0° C. for 1 week. It was important to allow this reaction to proceed under cool conditions as to avoid possible racemization of the chiral alpha center. The resulting N-Cbz-4-tosyl-L-proline benzyl ester was then separated by silica gel. The tosyl group was then displaced via nucleophilic substitution with reduced phenyl selenide, prepared by reduction of diphenyldiselenide using $NaBH_4$ (sodium borohydide) in tert-butanol at reflux. The isolated phenylseleno proline was then oxidized in an elimination reaction using $H_2O_2$ in $CH_2Cl_2$ at 0° C. to produce the fully protected 3,4-dehydro-L-proline 12. It was extremely important to perform this reaction in cold, dilute conditions to avoid overheating and a possible $H_2O_2$ driven explosion. The protected 3,4-dehydro-L-proline 12, once isolated, was then treated with mCPBA (meta-chloro-peroxybenzoic acid) in $CH_2Cl_2$ at reflux to give the protected trans- and cis-3,4-epoxy-prolines at ratios of 6:4 respectively. The trans- and cis-epoxides were efficiently isolated by silica gel with overall modest yield of 53% for the entire synthetic scheme. The epoxide intermediates 13a or 13b were then used directly in an acid catalyzed ring opening addition step (Scheme 3) or converted to the free acid prior to an addition under basic conditions (Scheme 4).

Scheme 1: Synthesis of N-Cbz-trans and cis-3,4-epoxy-proline-benzyl ester 13a & 13b.

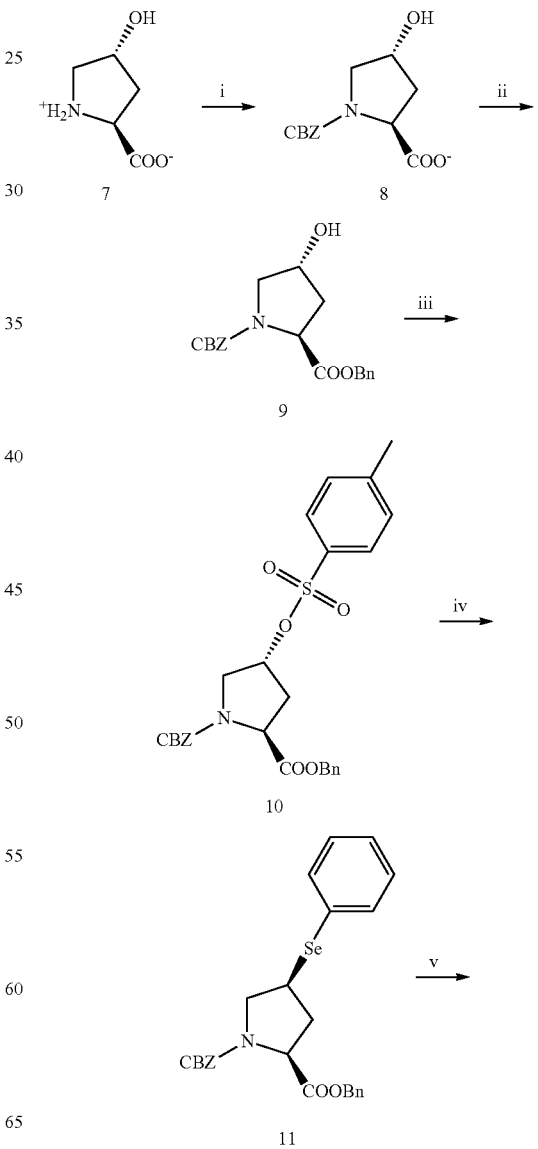

-continued

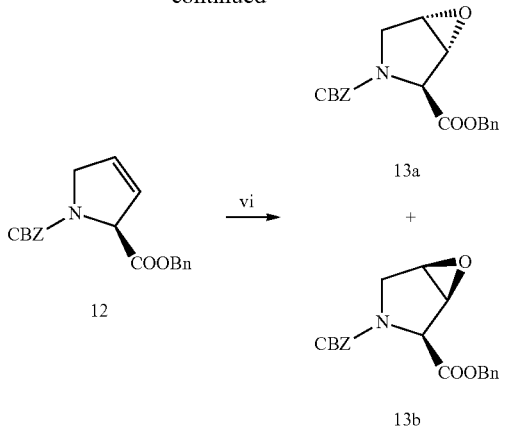

(i) benzylchloroformate, H₂O, NaOH, rt; (ii) benzylbromide, Na₂CO₃, NaI, rt; (iii) p-toluenesulfonyl-Cl, pyridine, 0° C.; (iv) tBuOH, phenylselenide, reflux; (v) CH₂Cl₂, H₂O₂, 0° C.- room temperature; (vi) mCPBA, CH₂Cl₂, reflux.

Example 2

Synthesis of (2S,3R,4R)—N-Benzyloxycarbonyl-3, 4-epoxyproline 13a and (2S,3R,4S)—N-Benzyloxy-carbonyl-3,4-epoxyproline benzyl ester 13b Similar synthesis reported: Robinson et al., *Tetrahedron* 54:981-996 (1998); Rüeger et al., *Can. J. Chem.* 60:2918-2920 (1982)).

N-Cbz-4-hydroxyproline 8: BRL: 247 trans-4-Hydroxyproline (27.5 g, 209.7 mmol) 7 was dissolved into 200 mL of 50% MeOH in water. This was then chilled on ice bath to 0° C. To this mixture was added 85.9 mL of benzyl chloroformate (0.252 mmol; 1.2 eq; 50% vol. in toluene) dropwise. Pellets of NaOH were added to maintain the pH at approximately 9-10 (monitored by litmus paper). The mixture was then allowed to warm to room temperature (22° C.). The mixture was allowed to stir over night at room temperature and the pH closely monitored and maintained at pH=10 by addition of NaOH pellets. The mixture was then diluted by addition of 200 mL water and then extracted with 3×200 mL toluene (to remove remaining benzyl chloroformate). The aqueous layer was then salted with NaCl until saturated and the pH was adjusted to approximately 2 by addition of HCl conc. This was then extracted with 4×200 mL of ethyl acetate. The ethyl acetate washes were then combined and concentrated via rotovap, leaving an oil residue. Dichloromethane (50 mL) was added 4 times to remaining oil and then removed by vacuum. Hexanes (50 mL) was then added to the oil and again removed by vacuum, leaving a sticky foam N-Cbz-4-hydroxyproline crude (quantitative yield) which was then used without any further purification. This residue can also be recrystallized in 10:1, hexanes:CH₂Cl₂. $^1$H and $^{13}$C NMR spectra were in agreement with $^1$H and $^{13}$C NMR spectra previously reported [Robinson. et al 1998].

N-Cbz-4-hydroxyproline benzyl ester 9: BRL: 151

N-Cbz-4-hydroxyproline (40.00 g, 150.8 mmol) 8 was dissolved into 110 mL DMF. To this mixture was added 45.85 g of K₂CO₃ (2.2 eq; 331.7 mmol) and 2.30 g of NaI (0.1 eq). The reaction flask was purged with argon and 55.4 mL of benzylbromide (3 eq; 452 mmol) was added dropwise. This mixture was then stirred over night at room temperature. The reaction was then diluted with 300 mL ethyl acetate and washed with water (8×200 mL) to remove DMF, followed by washing with 100 mL brine. The organic layer was dried over Na₂SO₄ and concentrated to a yellow oil. The oil was then washed several times with 100 mL hexanes to remove any remaining benzyl bromide and then separated by silica gel in hexanes:ethyl acetate, 3:2, isolating N-Cbz-4-hydroxyproline benzyl ester at R$_f$=0.25 in nearly quantitative yield. $^1$H and $^{13}$C NMR spectra were in agreement with $^1$H and $^{13}$C NMR spectra previously reported (Robinson et al., 1998).

N-Cbz-4-p-toluenesulphonyl-ether-proline-benzyl ester 10: BRL: 205

N-Cbz-4-hydroxyproline benzyl ester (21.77 g, 61.3 mmol) 9 was dissolved into 150 mL cold pyridine 0° C. Immediately, 12.976 g of p-toluenesulfonyl chloride (1.1 eq.; 67.4 mmol) was added. The flask containing this mixture was then purged with argon and placed into a refrigerator at approximately 0° C. for one full week with occasional vortex. After one week it was observed that a significant amount of pyridine-HCl had formed and all the starting material appeared to have been consumed (determined by TLC). The mixture was then taken up into 100 mL Et₂O and 50 mL ethyl acetate and washed 2×100 mL cold 5% HCl and then 3×200 mL water. The organic layers were combined and dried over Na₂SO₄, filtered and concentrated to an oil. The product N-Cbz-4-p-toluenesulphonyl-ether-proline-benzyl ester 10 was isolated by silica gel in hexanes/ethyl acetate, 7:3; R$_f$=0.25 to recover 28.05 g, (90% yield). $^1$H and $^{13}$C NMR spectra were in agreement with $^1$H and $^{13}$C NMR spectra previously reported [Robinson. et al 1998].

N-Cbz-4-phenylseleno-L-proline-benzyl ester 11: BRL: 211

Diphenyldiselenide (9.504 g, 0.6 eq.; 30.2 mmol) was dissolved into 60 mL of tBuOH and purged of air by vacuum and replaced with argon. The solution was brought to a reflux where of NaBH₄ (2.293 g, 1.2 eq, 60.3 mmol) was added slowly over 15 min. This mixture was refluxed for 30 min. until the mixture had turned completely white. To this was added N-Cbz-4-p-toluenesulphonyl-ether-proline-benzyl ester 10 (25.6 g, 50.2 mmol) in 40 mL tBuOH. The reflux was continued under argon for approximately 3 h then allowed to cool to room temperature. The mixture was then diluted with 200 mL ethyl acetate and washed 3×250 mL water followed by 100 mL brine then treated with MgSO₄ to dry, filtered and concentrated to a crude oil. The product N-Cbz-4-phenylseleno-L-proline-benzyl ester 11 was isolated by silica gel 3:1 hexanes:ethyl acetate at R$_f$=0.3, recovering 22.21 g, (89% yield). $^1$H and $^{13}$C NMR spectra were in agreement with $^1$H and $^{13}$C NMR spectra previously reported (Robinson et al., 1998).

N-Cbz-3,4-dehydro-L-proline-benzyl ester 12: BRL: 212

N-Cbz-4-phenylseleno-L-proline-benzyl ester 11 (22.11 g, 44.7 mmol) was dissolved in 80 mL CH₂Cl₂ (warning! explosive conditions: needs to be performed in more dilute conditions than in this example or approximately 200 mL per 10 g of starting material). The solution was chilled on ice bath over argon and 4.9 mL pyridine (1.34 eq.; 60 mmol) was added followed by addition of 11.50 mL 30% $H_2O_2$ (2.5 eq.; 112.0 mmol) drop wise. The solution was gradually allowed to return to room temperature over the course of 1 h where it was stirred for 2.5 h. The solution, now brown in color, was diluted with 100 mL $CH_2Cl_2$ and washed with 100 mL of 5% $NaHSO_4$, 2×50 mL $NaHCO_3$, and 3×150 mL water. The organic layer was dried over $Na_2SO_4$ and filtered. A total of 12.02 g of N-Cbz-3,4-dehydro-L-proline-benzyl ester 12 was isolated by silica gel in mobile phase of 4:1 hexanes/etheyl acetate; $R_f$=0.15; (80% yield). $^1$H and $^{13}$C NMR spectra were in agreement with $^1$H and $^{13}$C NMR spectra previously reported (Robinson et al., 1998).

N-Cbz-trans-3,4-epoxy-L-proline-benzyl ester 13a and N-Cbz-cis-3,4-epoxy-L-proline-benzyl ester 13b: BRL: 287

N-Cbz-3,4-dehydro-L-proline-benzyl ester (9.80 g, 29.0 mmol) 12 was dissolved into 12 mL $CH_2Cl_2$. To this was added mCPBA (14.3 g, 70% weight; 58.1 mmol; 2 eq.) and 2,8-di-tert-butyl-4-methylphenol (30 mg, radical inhibitor). The solution was heated to reflux and allowed to stir overnight under argon balloon. An additional 1 eq. of mCPBA (7.15 g) was added and the solution was allowed to reflux again overnight. The flask was then placed on an ice bath where a white precipitate formed and was subsequently filtered using cold dichloromethane to wash. The $CH_2Cl_2$ was removed by rotovap leaving a white solid residue. The residue was taken up into 150 mL $Et_2O$ and washed 8 times with 100 mL (aq) $NaHCO_3$, 2×100 mL water, and 100 mL brine then dried over $Na_2SO_4$ and filtered. The remaining oil was then separated by silica gel in 4:1 hexanes/ethyl acetate. The trans isomer 5.228 g, N-Cbz-3,4-trans-epoxy-L-proline-benzyl ester 13a, was isolated at $R_f$=0.2 and the cis isomer 4.100 g, N-Cbz-3,4-cis-epoxy-L-proline-benzyl ester 13b being isolated at $R_f$=0.1, a total yield of 91% and ratio of 5:4 trans/cis. $^1$H and $^{13}$C NMR spectra for both diastereomers were in agreement with $^1$H and $^{13}$C NMR spectra previously reported (Robinson et al., 1998).

Example 3

Procedure for alternative synthesis of N-Cbz-3,4-dehydro-L-proline-benzyl ester 12 or N-Cbz-3,4-dehydro-L-proline 12a In searching for a synthetic route to produce 3,4-dehydro-L-prolines with fewer synthetic steps than through tosyl and selenide intermediates (Scheme 1), we designed an alternative route by using a xanthate intermediate 9a or 10a. We reasoned that the free acid 3,4-dehydro-proline 12a or benzyl ester protected 3,4-dehydro-proline 12 could be generated via microwave elimination of a methyl xanthate 9a or 10a as seen in Scheme 2. Briefly, N-Cbz-trans-4-hydroxy-L-proline 8 was used in an esterification with $CS_2$ and iodomethane using NaH as a base in THF to produce N-Cbz-trans-4-methylxanthate-L-proline 9a. From this the benzyl-ester derivative 10a (N-Cbz-trans-4-methylxanthate-L-proline benzyl ester) were synthesized under standard conditions as shown in Scheme 1 (ii). Both methyl xanthate conjugated prolines 9a and 10a were successfully eliminated under open container pyrolysis like conditions using microwave radiation, sodium carbonate as a base, and water as a semi-solvent to produce 3,4-dehydroprolines 12a and 12.

Scheme 2: Synthesis of 3,4-dehydroprolines.

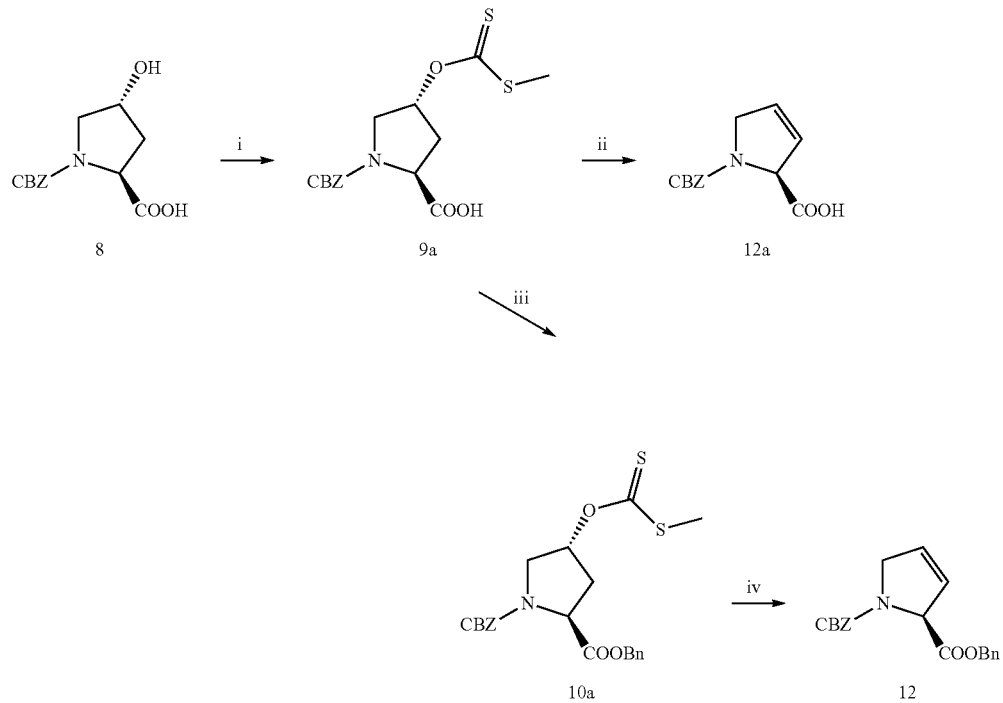

(i) NaH, THF, $CS_2$, iodomethane, 22° C.; (ii) $H_2O$, $NaHCO_3$, microwave 100° C.; (iii) benzylbromide, $Na_2CO_3$, NaI, rt; (iv). $H_2O$, $Na_2CO_3$, microwave 100° C..

N-Cbz-trans-4-methylxanthate-L-proline 9a: BRL: 131

To 3.635 g (13.7 mmol) of N-Cbz-trans-4-hydroxy-L-proline 8 was added 35 mL of dry THF and slow addition of 1.73 g of NaH (95%; 5 eq.; 68.5 mmol). The solution was then purged with argon and allowed to stir for 10 min. To this was added 4.14 mL of $CS_2$ (68.5 mmol; 5 eq.) and allowed to stir for 2 h at rt, forming the xanthate salt. To the flask was then added 2.87 mL of iodomethane (48.0 mmol; 3.5 eq) and allowed to stir overnight at room temperature and under argon balloon. The reaction mixture was then chilled on ice bath where approximately 10 mL of glacial acetic acid was added to quench the excess NaH (heavy white precipitate forms). The quenched reaction mixture was then diluted with 100 mL of $Et_2O$, filtered using excess ether, and then concentrated by rotovap, leaving a yellow/brown oil. The final product, 4.19 g, N-Cbz-trans-4-methylxanthate-L-proline 9a was isolated by silica gel at $R_f$=0.15 in 97% $CH_2Cl_2$, 2% MeOH 1% AcOH, 70% yield as a crude mixture which was used in the next step without further purification.

N-Cbz-trans-4-methylxanthate-L-proline benzyl ester 10a: BRL: 133

To 3.40 g (9.57 mmol) of N-Cbz-trans-4-methylxanthate-L-proline 9a was added 30 mL DMF, 2.64 g (19.1 mmol; 2 eq.) of $K_2CO_3$, and 143 mg of NaI (0.957 mmol; 0.1 eq.). The reaction flask was purged with argon, and 3.58 mL of benzyl bromide (98%; 29.3 mmol; 3 eq). The mixture was allowed to stir at room temperature for 24 h under argon balloon. The solution was taken up into 100 mL ethyl acetate and then washed with $H_2O$ (4×300 mL). The organic layer was separated and dried with $MgSO_4$, filtered and concentrated to a yellow oil. The final product N-Cbz-trans-4-methylxanthate-L-proline benzyl ester 10a was isolated by silica gel in 4:1 hexanes/ethyl acetate, $R_f$=0.25, with a quantitative yield. $^1$H-NMR (400 MHz, $CDCl_3$) δ 7.40-7.20 (m, 10H), 5.95 (d, J=2.2 Hz, 1H), 5.25-5.16 (m, 1H), 5.17 (s, 1H), 5.07 (s, 1H), 5.00 (s, 1H), 4.62-4.52 (ddd, J=44.0$_\Sigma$, 28.6, 8.1 Hz, 1H), 3.99 (d, J=12.4 Hz, 1H), 3.88 (s, 1H), 2.67-2.59 (m, J=8.1, 2.2 Hz, 1H), 2.53 (s, 3H), 2.36 (m, J=8.1, 2.1 Hz, 1H).

N-Cbz-3,4-dehydro-L-proline 12a: BRL: 177

A pressure flask containing a mixture of 0.240 g (0.675 mmol) of N-Cbz-trans-4-methylxanthate-L-proline 9a, 1 mL ethanol, 10 mL water, and 42 mg $Na_2CO_3$ (anhydrous; 0.5 eq) was placed into a microwave on medium (100 watt noncontinous radiation; retail purchased Sunbeam microwave) for approximately 3-4 min. The contents were allowed to cool to room temperature (keep in hood; xanthate elimination creates a very undesirable smell). The reaction mixture was diluted with 20 mL water and the pH was adjusted to approximately 2-3 by addition of $H_3PO_4$. The aqueous mixture was salted with NaCl until saturated, then extracted with 3×50 mL ethyl acetate, dried with $Na_2SO_4$, and concentrated to a crude orange colored oil. The product N-Cbz-3,4-dehydro-L-proline 12a was isolated by silica gel (96% $CH_2Cl_2$, 3% MeOH, 1% AcOH, $R_f$=0.25) for 0.120 g of total recovered product, a 72% yield. $^1$H-NMR (400 MHz, $CDCl_3$) δ 9.91 (b, 1H [COOH]), 7.37-7.27 (m, 5H), 5.98-5.93 (ddd, J=21.3$_\Sigma$, 14.9, 6.11, 2.0 Hz 1H), 5.82-5.75 (ddd, J=35.7$_\Sigma$, 29.6, 6.1, 2.2 Hz, 1H), 5.25-5.13 (m, J=1.7 Hz, 2H), 5.06 (dd, J=4.0$_\Sigma$, 2.2 Hz, 1H), 4.32-4.27 (m, J=2.2, 2.0, 1.7 Hz, 2H).

N-Cbz-3,4-dehydro-L-proline benzyl ester 12: BRL: 195

A pressure flask containing a mixture of 0.551 g (1.28 mmol) of N-Cbz-trans-4-methylxanthate-L-proline benzyl ester 10a, 1 mL ethanol, 10 mL water, and 68 mg $Na_2CO_3$ (anhydrous; 0.5 eq; 0.64 mmol) was placed into a microwave on medium low (100 watt noncontinous radiation, retail purchased Sunbeam microwave) for approximately 7 min. The contents were allowed to cool to room temperature (keep in hood). The reaction mixture was diluted with 20 mL water and then extracted with 3×50 mL $Et_2O$, washed 2×50 mL water, dried over $Na_2SO_4$, and concentrated to a crude orange oil. The product N-Cbz-3,4-dehydro-L-proline benzyl ester 12 was isolated by a silica gel (70% hexanes, 30% ethyl acetate, $R_f$=0.25) for 0.362 g of total recovered product, an 84% yield.

Example 4

Procedure for Synthesis of Ether Substituted Prolinols

Figure 2:
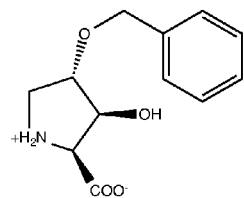
FIG. 2 shows the chemical structures of exemplary ether substituted prolinol compounds of the invention.
Figure 2:
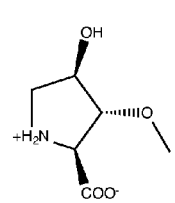
Figure 2:
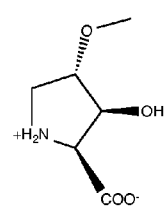
Figure 2:
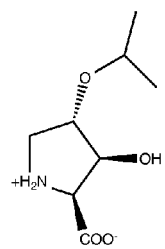
Figure 2:
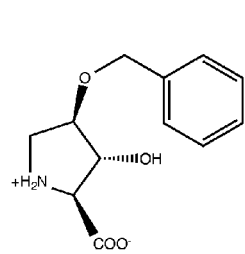
Figure 2:
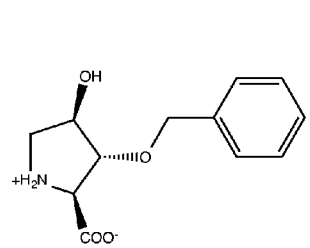
Figure 2:
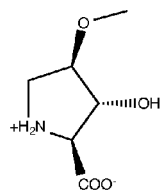
Figure 2:
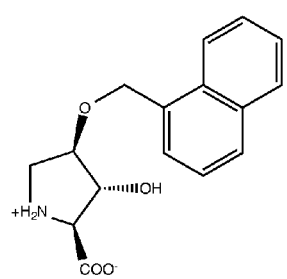
Figure 2:
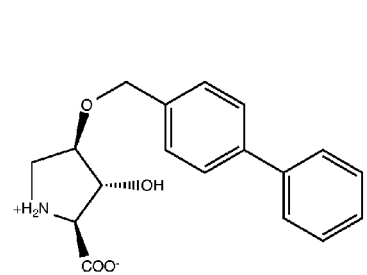
Figure 2:
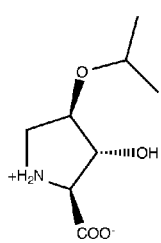
Figure 2:
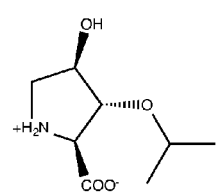
Figure 2:
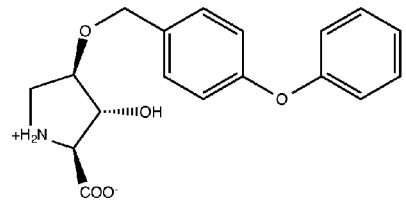
Figure 3:
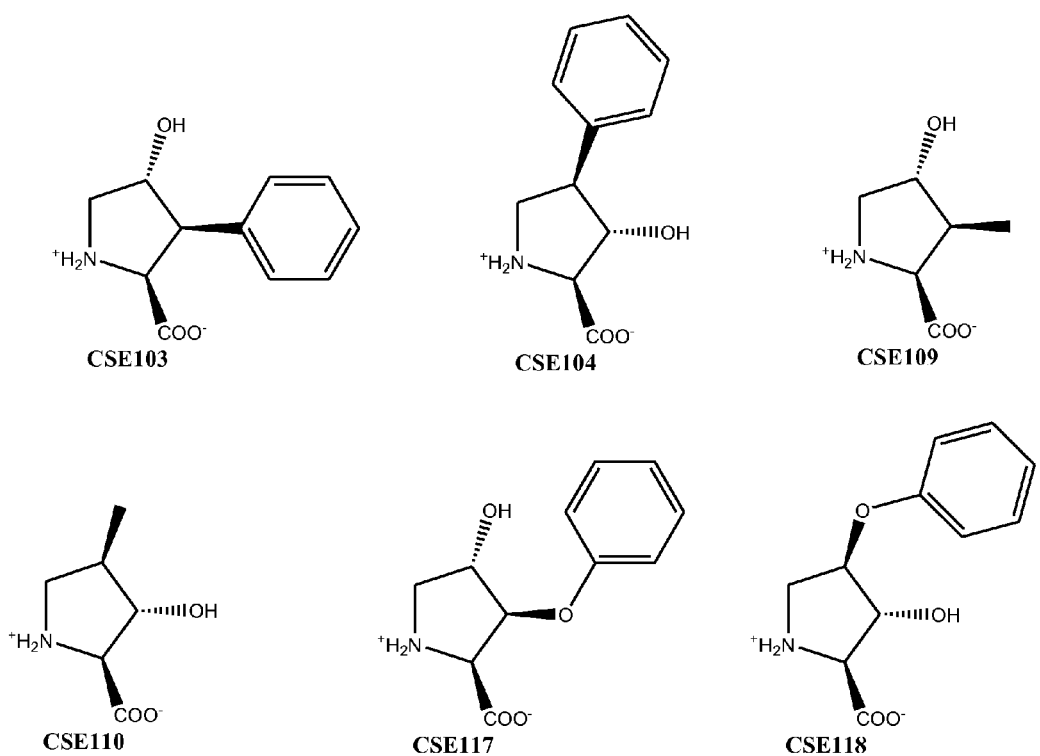
FIG. 3 shows the chemical structures of exemplary alkyl, aryl and phenol-ether prolinol compounds of the invention.

A series of ether substituted prolinols (FIG. 2) were synthesized to act as selective inhibitors of the ASC transporters. This was accomplished by a $BF_3.Et_2O$ catalyzed nucleophillic ring opening of the epoxide 13a or 13b by an alcohol and subsequent deprotection via a 10% Pd/C catalyzed hydrogenation to produce trans-hydroxy derivative 15 or cis-hydroxy derivatives 17a & 17b (Scheme 3). Under optimized conditions, $BF_3.Et_2O$ as a catalyst provided far superior product yields (quantitative) as opposed to using toluene sulfonic acid which produced multiple undesired products, including nucleophillic addition of the tosyl (tosic acid) group itself as a major product. It was also observed that ring opening of trans-epoxide 13a under these conditions produced exclusively one regioisomer, the N-Cbz-trans-3-hydroxy-cis-4-ether-L-proline benzyl ester 14. Whereas the ring opening of the cis-epoxide 13b produced both regioisomers 16a & 16b in ratios, 10:1, that strongly favored the 3-positioned alcohol 16a, consistent with azide or HCl ring opening of these epoxides (12, 14). Separation of these two regioisomers was carried out by reverse phase HPLC after the addition step following hydrolysis of the benzyl ester with KOH or just after hydrogenation depending upon the ether R group present.

Scheme 3: Synthesis of ether substituted prolinols.

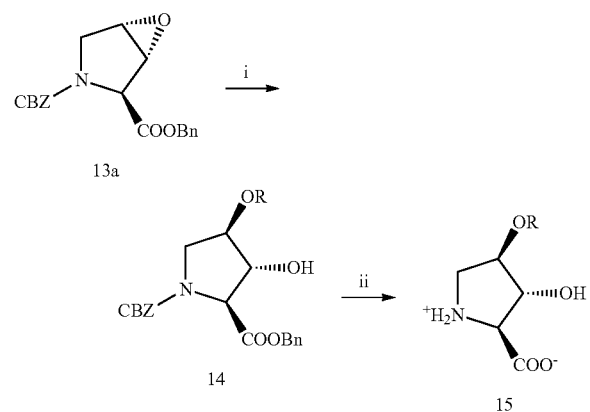

-continued

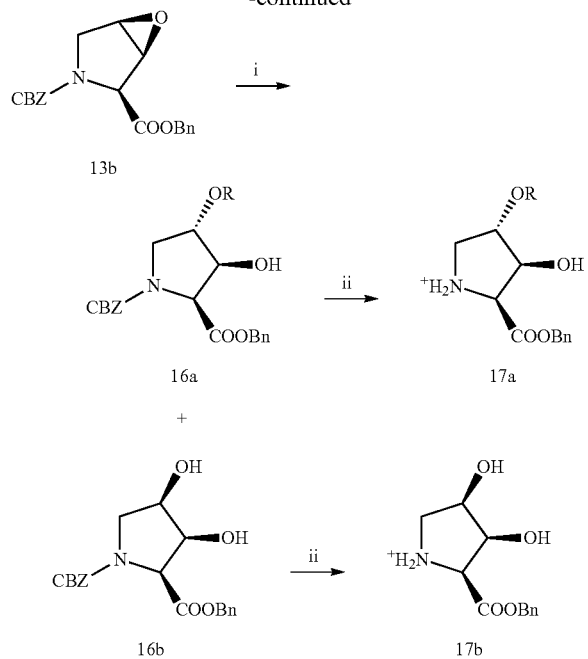

R = any group
(i) BF₃·Et₂O, CH₂Cl₂, desired alcohol, 22° C.;
(ii) 10% Pd/C (10% weight. eq.), H₂, MeOH, H₂O, NH₄OAc.

N-Cbz-trans-3-hydroxy-cis-4-methoxy-L-proline benzyl ester: BRL: 294

To 0.514 g (1.45 mmol) of N-Cbz-trans-3,4-epoxy-L-proline benzyl ester 13a was added 5 mL of dry (MgSO₄ treated) CH₂Cl₂ and 2.0 mL absolute MeOH (approximately 34 eq.; 50 mmol). The flask was capped, purged with argon and chilled on an ice bath with argon balloon. Once cooled, 1.15 mL of BF₃.Et₂O (48%; 3.0 eq.; 4.36 mmol) was added to the mixture. The mixture was allowed to return to room temperature and stir overnight. The reaction mixture was quenched by the addition of 20 mL saturated NaHCO₃ solution and allowed to stir for approximately 30 min. The mixture was then diluted with 100 mL CH₂Cl₂, washed with 3×100 mL water, 50 mL brine, dried over Na₂SO₄ and concentrated by rotovap to a foam. The final product N-Cbz-trans-3-hydroxy-cis-4-methoxy-L-proline benzyl ester, 467 mg, and unreacted epoxide starting material, 115 mg, were isolated by silica gel (75% hexanes, 25% ethyl acetate, $R_f$ product=0.1; $R_f$ epoxide=0.3) for a total yield of 83% product and complete recovery in molecular equivalents of unreacted starting material. The material was used in the next step without further purification.

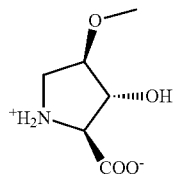

CSE115

Chemical Formula: C₆H₁₁NO₄
Molecular Weight: 161.16 trans-3-hydroxy-cis-4-methoxy-L-proline: BRL: 298/CSE115

To 0.417 g (1.08 mmol) of Cbz-3-trans-hydroxy-4-cis-methoxy-L-proline benzyl ester was added 4 mL methanol which was then transferred to a pressure flask containing 42 mg of 10% Pd/carbon (0.1 eq. weight), 1 mL water and 42 mg (approximately 0.5 eq.) NH₄OAc. The pressure flask was connected to a Parr shaker, the air was removed by vacuum and replaced with 40 psi H₂ (g). The assembly was allowed to shake for 3 h. The pressure flask was vented and the solution diluted with 10 mL water and then filtered through CM-cellulose (carboxy-methyl-cellulose), using excess water for consecutive washes. The filtrate was then frozen and placed onto a lyophilizer until dry. The remaining residue was washed 3×10 mL ethyl acetate/CH₂Cl₂ (1:1), and dried leaving 0.172 g of a white solid, trans-3-hydroxy-cis-4-methoxy-L-proline with a yield of 99%. HRMS m/e calcd. For C₆H₁₂NO₄=162.0749. found 162.0766.

N-Cbz-cis-3-hydroxy-4-trans-isopropoxy-L-proline: BRL: 305

To 0.407 g (1.15 mmol) of N-Cbz-cis-3,4-epoxy-L-proline benzyl ester 13b was added 5 mL (dry MgSO₄ treated) CH₂Cl₂ and 2 mL isopropanol (approximately 23 eq.; 26 mmol). The flask was purged with argon and cooled on ice bath for 10 min. Once cooled, 0.910 mL of BF₃.Et₂O (48%; 3 eq.; 3.45 mmol) was added dropwise and the solution was allowed to return to room temperature. After stirring overnight the reaction was quenched by the addition of 20 mL saturated solution of NaCO₃. This was then further diluted with 20 mL CH₂Cl₂ and washed 3×100 mL water and 1×100 mL brine, dried with Na₂SO₄ and concentrated by rotovap. The two regioisomer products N-Cbz-cis-3-hydroxy-trans-4-isopropoxy-L-proline benzyl ester and N-Cbz-trans-3-isopropoxy-cis-4-hydroxy-L-proline benzyl ester, 0.440 g, were isolated together by silica gel (3:1 hexanes:EtOAc, $R_f$=0.20) a 92% yield. The material as a regioisomer mixture was used in the next step without further purification. To 0.400 g (0.967 mmol) of N-Cbz-cis-3-hydroxy-trans-4-isopropoxy-L-proline benzyl ester and N-Cbz-trans-3-isopropoxy-cis-4-hydroxy-L-proline benzyl ester was added 10 mL THF, 1 mL water and 81 mg KOH (1.5 eq.; 1.45 mmol). The mixture was allowed to stir for 2 h at room temperature until complete, as determined by TLC (50% hexanes, 49% ethyl acetate, 1% AcOH). The mixture was concentrated to an oil by rotovap and diluted with 20 mL water. The pH of solution was adjusted to approximately 2 by addition of H₃PO₄ and NaCl was added until saturated. The mixture was then extracted with 3×100 mL EtOAc. The separated organic layers were combined, dried with Na₂SO₄, filtered and concentrated to a residue. The free acid products, 280 mg (0.866 mmol; 89% yield), were separated by silica gel (60% hexanes, 39% ethyl acetate, 1% AcOH, $R_f$=0.1) and again concentrated. A portion of the regioisomer mixture were isolated by reverse phase HPLC (C18, 250 mm×21.2 mm, 10μ) (85% 0.05 M NH₄OAc, 15% acetonitrile, 9 mL/min) at retention times of 48 min for N-Cbz-cis-3-hydroxy-4-trans-methoxy-L-proline & 52 min. for the other isomer and concentrated by freezing/lyophilization. The material was used in the next step without further purification.

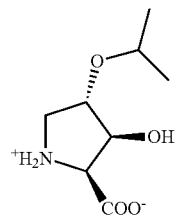

Chemical Formula: C₈H₁₅NO₄
Molecular Weight: 189.21

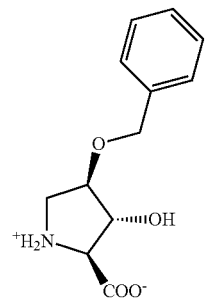

Chemical Formula: C₁₂H₁₅NO₄
Molecular Weight: 237.25 cis-3-hydroxy-trans-4-isopropoxy-L-proline: BRL: 305/CSE127

To 21.0 mg (0.0650 mmol) of N-Cbz-cis-3-hydroxy-4-trans-isopropoxy-L-proline was added 3 mL MeOH and 1 mL water. This was transferred to a pressure flask containing 5 mg of wet 10% (0.25 eq. weight) Pd/carbon and 5 mg (0.5 eq) NH₄OAc. The reaction flask was placed onto a Parr shaker, the air was removed by vacuum and replaced by 40 psi H₂ (g). The flask was allowed to shake for 8 h where the flask was vented and mixture was diluted with approximately 20 mL water. The contents were then filtered through CM-cellulose using excess water for consecutive washes. The filtrate was frozen and lyophilized to a white solid and washed with EtOAc/CH₂Cl₂ 1:1 (3×20 mL) and dried by rotovap leaving a white solid; 11.6 mg of cis-3-hydroxy-trans-4-isopropoxy-L-proline a 94% yield. HRMS m/e calcd. For C₈H₁₆NO₄=190.1079. found 190.1092.

N-Cbz-trans-3-hydroxy-cis-4-benzyloxy-L-proline benzyl ester: BRL: 288

To 0.564 g (1.59 mmol) of N-Cbz-trans-3,4-epoxy-L-proline benzyl ester 13a was added 5 mL of dry (MgSO₄ treated) CH₂Cl₂ and 2.5 mL benzyl alcohol (approximately 15 eq; 24 mmol) (treated with molecular civs). The flask was capped, purged with argon and chilled on an ice bath under argon balloon. Once cooled, 1.26 mL (48%; 3 eq.; 4.78 mmol) of BF₃.Et₂O was added to the mixture. The mixture was allowed to return to room temperature and stir for 48 h. The reaction was quenched by the addition of 40 mL saturated NaHCO₃ solution and allowed to stir for 30 min. The mixture was then diluted with 100 mL CH₂Cl₂, washed water (2×200 mL), washed with 50 mL brine, dried over Na₂SO₄ and concentrated to a white residue by rotovap. The final product N-Cbz-trans-3-hydroxy-cis-4-benzyloxy-L-proline benzyl ester, 0.710 mg (1.54 mmol), was isolated by silica gel (85% hexanes, 15% ethyl acetate, R_f=0.10) for a total yield of 96%. The material was used in the next step without further purification.

trans-3-hydroxy-cis-4-benzyloxy-L-proline: BRL: 289/CSE121

To 0.710 g (1.56 mmol) of Cbz-3-trans-hydroxy-4-cis-benzyloxy-L-proline benzyl ester was added 5 mL methanol which was then transferred to a pressure flask containing 71 mg (0.1 eq. weight) of 10% Pd/carbon, 0.3 mL water and 59.3 mg (0.5 eq.; 0.769 mmol) NH₄OAc. The pressure flask was connected to a Parr shaker, the air was removed by vacuum and replaced with 40 psi H₂ (g). The assembly was allowed to shake for 3 h. The pressure flask was vented and the contents were diluted with 30 mL water and filtered through CM-cellulose using excess water for consecutive washes. The filtrate was then frozen and placed onto a lyophilizer until dry. The remaining residue was washed EtOAc/CH₂Cl₂ 1:1 (3×20 mL), and dried leaving 0.340 mg of a white crude residue trans-3-hydroxy-cis-4-benzyloxy-L-proline, a yield of 93%. A portion of this crude product was isolated by reverse phase HPLC (C18, 250 mm×21.2 mm, 10μ) (92% 0.05 M NH₄OAc, 8% acetonitrile, 9 mL/min) at a retention time of 42 min. The collected fractions containing the desired product were concentrated by freezing/lyophilization. Once dry, approximately 20 mL of water was added, the solution was again frozen and lyophilized until dry removing any remaining NH₄OAc. This was repeated until NH₄OAc was no longer present, leaving a white residue trans-3-hydroxy-cis-4-benzyloxy-L-proline, CSE 121. HRMS m/e calcd. For C₁₂H₁₆NO₄=238.1079. found 238.1094.

N-Cbz-cis-3-hydroxy-trans-4-benzyloxy-L-proline benzyl ester and N-Cbz-trans-3-benzyloxy-cis-4-hydroxy-L-proline benzyl ester: BRL: 264

To 0.484 g (1.37 mmol) of N-Cbz-cis-3,4-epoxy-L-proline benzyl ester 13b was added 5 mL of dry (MgSO₄ treated) CH₂Cl₂, 20 mL benzyl alcohol (treated with molecular civs), and 13.0 mg (0.10 eq) of p-toluensulfonic acid monohydrate. The mixture was heated to approximately 60'C and stirred for several days until the reaction appeared to be complete as determined by TLC (hexanes:ethyl acetate, 1:1, R_f=0.4). The solution was then allowed to cool to room temperature, diluted with 100 mL Et₂O and washed with water (3×100 mL). After drying with Na₂SO₄, the separated organic solution was filtered and run through a silica plug using 90% hexanes 10% ethyl acetate to remove most of the excess benzyl alcohol. The product was then eluted with 1:1 hexanes/ethyl acetate and concentrated. The final products N-Cbz-cis-3-hydroxy-trans-4-benzyloxy-L- proline benzyl ester and N-Cbz-trans-3-benzyloxy-cis-4-hydroxy-L-proline benzyl ester, 0.426 g (0.923 mmol), were isolated by silica gel (7:3 hexanes:ethyl acetate, $R_f$ product=0.15) for a total yield of 67% including both regioisomers. Note: this addition was repeated by using 3.0 eq. of $BF_3.Et_2O$ catalyst instead of tosic acid and under similar conditions as in the trans-epoxide-benzyl alcohol coupling. Yield improved dramatically, 197 mg of the two regioisomers were isolated starting from 160 mg of starting material, a 95% yield. The resulting products as a regioisomer mixture were used in the next step without further purification.

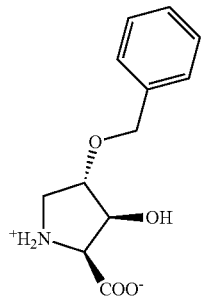

CSE113

Chemical Formula: $C_{12}H_{15}NO_4$
Molecular Weight: 237.25 cis-3-hydroxy-trans-4-benzyloxy-L-proline: BRL: 267/CSE113

To 0.426 g (0.923 mmol) of Cbz-3-trans-hydroxy-4-cis-benzyloxy-L-proline benzyl ester was added 5 mL methanol which was then transferred to a pressure flask containing 40 mg (0.1 eq. weight) of 10% Pd/carbon, 2 mL MeOH, 1 mL water and 36 mg (approximately 0.5 eq.; 0.47 mmol) of $NH_4OAc$. The pressure flask was connected to a Parr shaker, the air was removed by vacuum and replaced with 40 psi $H_2$ (g). The assembly was allowed to shake for 1.5 h where the reaction was complete as determined by TLC (7:3 hexanes/EtOAc). The pressure flask was vented and the contents were diluted with 30 mL water and filtered through CM-cellulose (carboxy-methyl-cellulose), using excess water for consecutive washes. The filtrate was then frozen and lyophilized until dry. The remaining residue was washed with EtOAc/$CH_2Cl_2$ 1:1 (3×20 mL), and dried leaving an 0.206 mg of an off-white solid, a mixture of cis-3-hydroxy-trans-4-benzyloxy-L-proline and trans-3-benzyloxy-cis-4-hydroxy-L-proline, and possibly 3,4 dihydroxy proline as a result of debenzylation. A portion of this crude product was isolated by reverse phase HPLC (C18, 250 mm×21.2 mm, 10μ) (92% 0.05 M $NH_4OAc$, 8% acetonitrile, 9 mL/min) and concentrated by lyophilization. Once dry, approximately 20 mL of water was added, the solution was again frozen and lyophilized until dry (removes remaining $NH_4OAc$). This was repeated until $NH_4OAc$ was no longer present, leaving cis-3-hydroxy-trans-4-benzyloxy-L-proline, CSE113. HRMS m/e calcd. For $C_{12}H_{16}NO_4$=238.1079. found 238.1064.

(2S,3R,4R)—N-Cbz-3-hydroxy-4-o-methyl-p-biphenyl-proline benzyl ester: BRL: 301

To 0.305 g (0.862 mmol) of N-Cbz-trans-3,4-epoxy-L-proline benzyl ester 13a was added 2 mL of dry ($MgSO_4$ treated) $CH_2Cl_2$ and 0.318 g (98%, 2.0 eq.; 1.72 mmol) of 4-biphenylmethanol. The flask was capped, purged with argon and chilled on an ice bath under argon balloon. Once cooled, 91 μL (48%; 0.4 eq.; 0.345 mmol) of $BF_3.Et_2O$ was added to the stirring solution. The mixture was allowed to return to room temperature and stir overnight. The reaction was quenched by the addition of 20 mL saturated $NaHCO_3$ solution and allowed to stir for an additional 30 min. The contents of the flask were then diluted with 100 mL $CH_2Cl_2$, washed with water (3×100 mL), washed with 50 mL brine, dried over $Na_2SO_4$ and concentrated to a white solid by rotovap. The final product (2S,3R,4R)—N-Cbz-3-hydroxy-4-o-methyl-p-biphenyl-proline benzyl ester, 0.395 mg (0.735 mmol), was isolated by silica gel (7:3 hexanes: EtOAc, $R_f$=0.1), a yield of 85%, and some remaining epoxide starting material. The product was used in the next step without further purification.

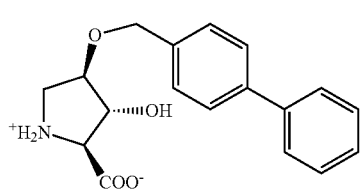

CSE131

Chemical Formula: $C_{18}H_{19}NO_4$
Molecular Weight: 313.35

(2S,3R,4R)-3-hydroxy-4-o-methyl-p-biphenyl-proline: BRL: 304/CSE131

To 0.105 g (0.195 mmol) of (2S,3R,4R)—N-Cbz-3-hydroxy-4-o-methyl-p-biphenyl-proline benzyl ester was added 5 mL methanol which was heated to dissolve and then transferred to a pressure flask containing 11 mg of 10% Pd/carbon (0.10 eq. weight), 8 mg (0.5 eq) $NH_4OAc$ and 0.5 mL water. The pressure flask was connected to a Parr shaker, the air was removed by vacuum and replaced with 40 PSI $H_2$ (g). The assembly was allowed to shake for 2 h until the reaction had completed as determined by TLC (50/49/1; hexanes/ethyl acetate/AcOH). The pressure flask was vented and the contents were diluted with 30 mL water, followed by filtration through CM-cellulose using excess water for consecutive washes. The filtrate was then frozen and lyophilized until dry. The remaining residue was washed EtOAc/$CH_2Cl_2$ 1:1 (3×20 mL), and dried over $Na_2SO_4$ leaving 51.0 mg of a white solid crude, primarily consisting of the desired prolinol product, a yield of 84%. A portion of this crude product was isolated by reverse phase HPLC (C18, 250 mm×21.2 mm, 10μ) (75% 0.05 M $NH_4OAc$, 25% acetonitrile, 9 mL/min) at a retention time of approximately 38 min. The collected fractions containing the desired prolinol were combined and concentrated by lyophilization. Once dry, 20 mL of water was added, the solution was again frozen and lyophilized until dry (removes remaining $NH_4OAc$). This was repeated until $NH_4OAc$ was no longer present, leaving a white residue (2S,3R,4R)-3-hydroxy-4-o-methyl-p-biphenyl-proline, CSE 131. HRMS m/e calcd. For $C_{18}H_{20}NO_4$=314.1392. found 314.1378.

Example 5

Procedure for Synthesis of Alkyl, Aryl or Phenol-Ether Prolinols

A considerable amount of time was spent in the discovery and optimization of synthesizing alkyl, aryl and phenol-ether substituted prolinols (Scheme 4). Generation of these targets via nucleophillic substitution under basic conditions required the free acid proline epoxide so as to avoid racemization of the chiral a center during the addition step (Scheme 3). This was accomplished by hydrolysis of the benzyl ester protection group of the proline olefin 12 to give the free acid olefin 12a. Epoxidation of the free acid olefin with mCPBA (meta-chloroperoxybenzoic acid) under $CH_2Cl_2$ reflux w/1% radical inhibitor produced the trans-epoxide 13c in excellent yields with no detectable cis-epoxide. Epoxidation by dimethyldioxirane or peracidic acid were also met with the same results, however, in lower overall yield.

Initial attempts to ring open the epoxide of 13c via nucleophillic addition using Grignard reagents or organolithiums alone or in preparations with soft lewis acids $CeCl_3$, CuBr (catalytic or stoichiometric, (including Gilman reagent ($R_2CuMgX$ or $R_2CuLi$)), or copper (1) acetate and even $SmI_2$ catalyzed Barbier addition were unsuccessful. The N-protected prolinol derivatives 18a and 18b were finally obtained from the epoxide by transformation of the organolithium reagent to a higher order cuprate, a rearrangement & complexation between 2 eq organolithium reagent and 1 eq CuCN in $Et_2O$ at approximately −40° C. (Scheme 4; iii). The prolinol products were isolated together by silica gel in yields of 90-95% with regioisomer ratio's of nearly 1:1.

Scheme 4: Synthesis of alkyl, aryl or phenol-ether prolinols.

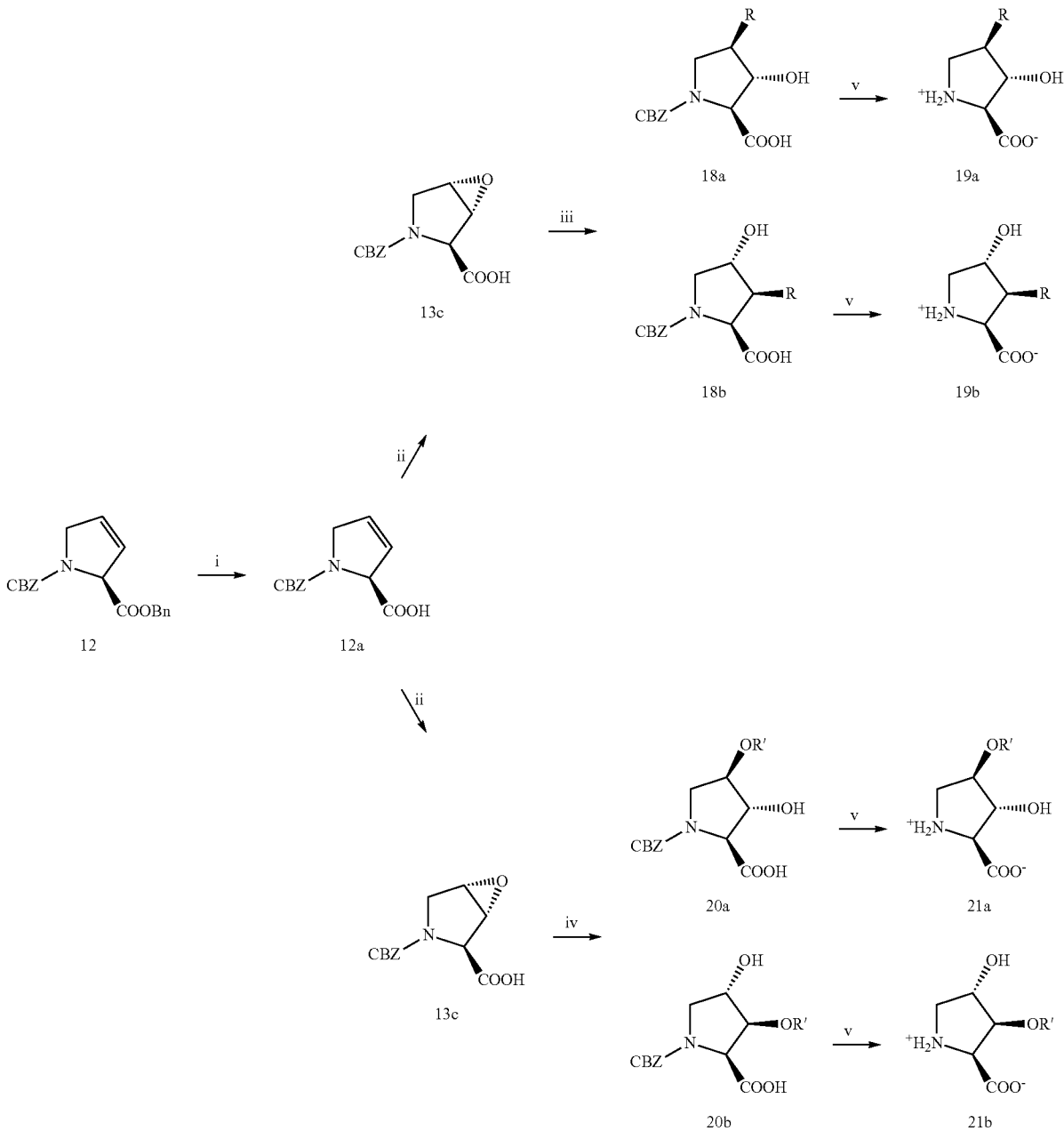

R = any group R' = any aryl group
(i) KOH, THF, $H_2O$, 22° C.; (ii) mCPBA, $CH_2Cl_2$; (iii) 2 eq. $R_2Cu(CN)Li_2$, $Et_2O$, -40° C., Inert atmosphere; (iv) $Na^+$ phenoxide in THF, room temperature; (v) 10% Pd/C (10% weight. eq), 40 psi $H_2$, MeOH, $H_2O$, $NH_4OAc$.

Similarly, the N-protected phenoxy prolinols 20a & 20b were synthesized from the free acid trans-epoxide 13c by the addition of a sodium phenoxide in THF at room temperature in regioisomeric ratios of 12:1, 3-hydroxy:4-hydroxy respectively, with overall respectable yields of 80-85%. Hydrogenolysis of the N-benzylcarbamate (Cbz) of protected prolinols 18a, 18b, 20a, or 20b via 10% Pd/carbon at 40 psi H$_2$(g) in methanol and subsequent separation of the regioisomers by reverse phase HPLC afforded the substituted prolinol products 19a, 19b, 21a and 21b.

N-Cbz-3,4-dehydro-L-proline 12a: BRL: 256

To 8.26 g (24.5 mmol) of N-Cbz-3,4-dehydro-L-proline benzyl ester 12 was added 50 mL THF, 5 mL H2O and 1.65 g (1.2 eq.; 29.4 mmol) KOH. The mixture was stirred for 2 h at room temperature. The mixture was concentrated by rotovap until dry in which 20 mL of water was added to dissolve the remaining residue. The pH of this mixture was adjusted to approximately 2 by addition of H$_3$PO$_4$ and NaCl was added until saturated. The contents were then extracted with EtOAc (3×200 mL). The ethyl acetate washes were combined and dried over Na$_2$SO$_4$, filtered and concentrated via rotovap to a yellow oil. The product, 6.05 g, N-Cbz-3,4-dehydro-L-proline 12a was isolated by silica gel (60% hexanes, 39% ethyl acetate, 1% AcOH; R$_f$=0.2) a quantitative yield. The material was used in the next step without further purification.

N-Cbz-trans-3,4-epoxy-L-proline 12a: BRL: 257

To 2.37 g (9.60 mmol) of N-Cbz-3,4-dehydro-L-proline 12a was added 20 mL CH$_2$Cl$_2$, 4.73 g (2 eq; 19.2 mmol) of 70% mCPBA, and 10 mg of (0.4% weight) 2,6-ditertbutyl-4-methyl phenol. The mixture was then refluxed under argon balloon overnight. Another 2.00 g (0.85 eq) of mCPBA was added to the reaction mixture and reflux was continued overnight. The mixture, now with white precipitate, was cooled over ice bath and filtered using 20 mL cold CH$_2$Cl$_2$ to wash. The product, 1.68 g of N-Cbz-trans-3,4-epoxy-L-proline 12a, was separated from the crude mixture consisting of excess mCPBA by a series of two silica gel columns; the first using 50% hexanes, 49% ethyl acetate, 1% AcOH as a mobile phase and the second using 96% CH$_2$Cl$_2$, 3% MeOH, 1% AcOH. Recovered epoxide product resulted in a yield of 67%, however, this represents only isolated product from two columns; a higher yield was possible with further purification via flash chromatography. The epoxide was used in the next step without further purification.

(2S,3S,4R)—N-Cbz-3-hydroxy-4-phenyl-proline and (2S,3S,4R)—N-Cbz-3-phenyl-4-hydroxy-proline: BRL: 263

To a flame dried round bottom flask was added 0.143 g (1.60 mmol; 3 eq) of CuCN (dried by high vacuum) and 5 mL dry (MgSO$_4$ treated) Et$_2$O. The flask was capped with a septum, purged air vacuum/argon balloon, and chilled to −40° C. (acetone bath/cold finger controlled). Once cooled, 1.60 mL (3.19 mmol; 6 eq) of 2.0 M phenyl-lithium in THF was added and the mixture was then allowed to warm to −10° C. and kept at this temperature for approximately 15 min. and then returned to −40° C. where 0.140 g (0.532 mmol) of N-Cbz-trans-3,4-epoxy-L-proline 13c in 2 mL dry (MgSO$_4$ treated) Et$_2$O also at −40° C. was added via sterile syringe. The flask was then allowed to warm to −10° C. and stir overnight. After stirring overnight, the reaction mixture was allowed to warm to 0° C. and was quenched by the addition of 20 mL saturated NH$_4$Cl. The mixture was then warmed to room temperature, the pH was adjusted to approximately 2 by addition of H$_3$PO$_4$ and salted with NaCl until saturated. The products were then extracted with EtOAc (3×100 mL). The organic washes were combined, dried over Na$_2$SO$_4$, and concentrated to a solid residue via rotovap. The products, 0.171 g of (2S,3S,4R)—N-Cbz-3-hydroxy-4-phenyl-proline and (2S,3S,4R)—N-Cbz-3-phenyl-4-hydroxy-proline were isolated as a regioisomer mixture by silica gel (50% hexanes, 49% ethyl acetate, 1% AcOH) for the first column followed by a second column (96% CH$_2$Cl$_2$, 3% MeOH, 1% AcOH), a 94% yield. The material was used in the next step without further purification.

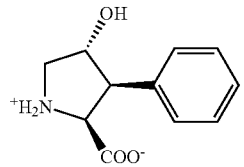

Chemical Formula: C$_{11}$H$_{13}$NO$_3$
Molecular Weight: 207.23

CSE103

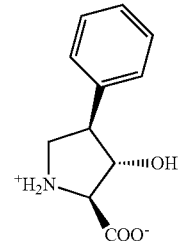

Chemical Formula: C$_{11}$H$_{13}$NO$_3$
Molecular Weight: 207.23

CSE104

(2S,3S,4R)-3-hydroxy-4-phenyl-proline and (2S,3S,4R)-3-phenyl-4-hydroxy-proline: BRL: 293/CSE104 and CSE103

To a 0.200 g (0.586 mmol) regioisomer mixture of (2S,3S,4R)—N-Cbz-3-hydroxy-4-phenyl-proline and (2S,3S,4R)—N-Cbz-3-phenyl-4-hydroxy-proline was added 3 mL MeOH. The mixture was transferred to a pressure flask containing 20.0 mg (0.1 eq weight) 10% Pd/carbon, 0.5 mL H$_2$O and 23.0 mg (0.5 eq: 0.298 mmol) NH$_4$OAc. The flask was placed on a Parr shaker, the air was removed by vacuum, and replaced by 40 psi H$_2$ (g). The apparatus was allowed to shake for 3 h at room temperature. The pressure flask was vented and the contents were diluted with 30 mL water and filtered through CM-cellulose using excess water for consecutive washes. The filtrate was then frozen and lyophilized until dry. The remaining residue was washed with EtOAc:CH$_2$Cl$_2$ 1:1 (3×20 mL), and dried leaving 0.108 mg (89% yield) of an off white solid, a crude mixture of (2S,3S,4R)-3-hydroxy-4-phenyl-proline and (2S,3S,4R)-3-phenyl-4-hydroxy-proline, regioisomeric ratio of 4.4:5.6 respectively. A portion of this crude was separated by reverse phase HPLC (C18, 250 mm×21.2 mm, 10μ) (92% 0.05 M NH$_4$OAc, 8% acetonitrile, 9 mL/min.). Fractions containing a specific isomer were combined and concentrated by lyophilization. Once dry, 20 mL of water was added to dissolve the remaining residue and the solution was again frozen and lyophilized until dry (removes remaining NH₄OAc). This was repeated until NH₄OAc was no longer present affording (2S,3S,4R)-3-hydroxy-4-phenyl-proline (CSE104) or (2S,3S,4R)-3-phenyl-4-hydroxy-proline (CSE103) as separate white solids. (2S,3S,4R)-3-phenyl-4-hydroxy-proline: CSE103 HRMS m/e calcd. For $C_{11}H_{14}NO_3$=208.0974. found 208.0996. (2S,3S,4R)-3-hydroxy-4-phenyl-proline: CSE104 HRMS m/e calcd. For $C_{11}H_{14}NO_3$=208.0974. found 208.0982.

(2S,3S,4R)—N-Cbz-3-hydroxy-4-phenoxy-proline and (2S,3S,4S)—N-Cbz-3-phenoxy-4-hydroxy-proline: BRL: 272

To a round bottom flask containing 1.00 g (7.34 eq; 10.6 mmol) of phenol in 4 mL dry THF (distilled) was added 0.245 g (0.95 eq) of NaH slowly. The flask was then cooled over ice bath and argon balloon. To this mixture was added 0.381 g (1.45 mmol) N-Cbz-trans-3,4-epoxy-L-proline 13c in 2 mL dry THF (distilled) at 0° C. The mixture was then allowed to warm to room temperature and then heated to reflux under condenser and argon balloon and stirred overnight. The reaction was then cooled on ice bath and 20 mL of 10% H₃PO₄ (aq) was added to quench the reaction. The mixture was then salted with NaCl until saturated and extracted with EtOAc (3×100 mL). The organic extracts were combined, dried over NaSO₄, and concentrated to a crude solid residue. The products, 0.330 g of (2S,3S,4R)—N-Cbz-3-hydroxy-4-phenoxy-proline and (2S,3S,4S)—N-Cbz-3-phenoxy-4-hydroxy-proline (12:1 respectively) were isolated as a regioisomer mixture by silica gel (50% hexanes, 49% ethyl acetate, 1% AcOH) and (96% CH₂Cl₂, 3% MeOH, 1% AcOH) from two columns to afford the product, a 64% yield not including recovered starting material. The regioisomer mixture was used in the next step without further purification.

4R)—N-Cbz-3-phenyl-4-hydroxy-proline was added 10 mL MeOH. The mixture was transferred to a pressure flask containing 83.0 mg (0.15 eq. weight) 10% Pd/carbon, 0.2 mL H₂O and 60.0 mg (0.5 eq: 0.77 mmol) NH₄OAc. The flask was placed on a Parr shaker, the air was removed by vacuum, and replaced by 50 PSI H₂ (g). The apparatus was allowed to shake overnight at room temperature. The pressure flask was vented and the contents were diluted with 30 mL water and filtered through CM-cellulose using excess water for consecutive washes. The filtrate was then frozen and lyophilized until dry. The remaining residue was washed with 1:1 EtOAc/CH₂Cl₂ (3×20 mL), and dried leaving 0.308 mg of an off-white solid, a crude mixture of (2S,3S,4R)-3-hydroxy-4-phenoxy-proline and (2S,3S,4S)-3-phenoxy-4-hydroxy-proline, regioisomeric ratio of 12:1 respectively and a (90% yield). Additionally, there was a large recovery of unreacted starting material from the organic washes. A portion of the product mixture was separated by reverse phase HPLC (C18, 250 mm×21.2 mm, 10µ) (92% 0.05 M NH₄OAc, 8% acetonitrile, 9 mL/min). Collected fractions containing a single isomer were combined and concentrated by lyophilization. Once dry, 20 mL of water was added to redissolve the remaining residue and the solution was again frozen and lyophilized until dry (removes remaining NH₄OAc). This was repeated until NH₄OAc was no longer present leaving (2S,3S,4R)-3-hydroxy-4-phenoxy-proline (CSE118) or (2S,3S,4S)-3-phenoxy-4-hydroxy-proline (CSE117) as a white solid. (2S,3S,4S)-3-phenoxy-4-hydroxy-proline: CSE117 HRMS m/e calcd. For $C_{11}H_{14}NO_4$=224.0923. found 223.0911. (2S,3S,4R)-3-hydroxy-4-phenoxy-proline: CSE118 HRMS m/e calcd. For $C_{11}H_{14}NO_4$=224.0923. found 224.0937.

Example 6

Procedure for synthesis of 4,4-alkyl-hydroxy-L-prolines

CSE117

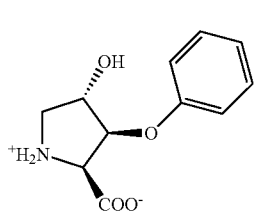

Chemical Formula: $C_{11}H_{13}NO_4$
Molecular Weight: 223.23

CSE118

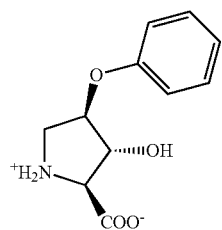

Chemical Formula: $C_{11}H_{13}NO_4$
Molecular Weight: 223.23

(2S,3S,4R)-3-hydroxy-4-phenoxy-proline and (2S,3S,4S)-3-phenoxy-4-hydroxy-proline: BRL: 279/CSE118 and CSE117

To a 0.550 g (1.54 mmol) regioisomer mixture of (2S,3S,4R)—N-Cbz-3-hydroxy-4-phenyl-proline and (2S,3S, Scheme 5: Synthesis of 4-substituted-4-hydroxy-prolines.

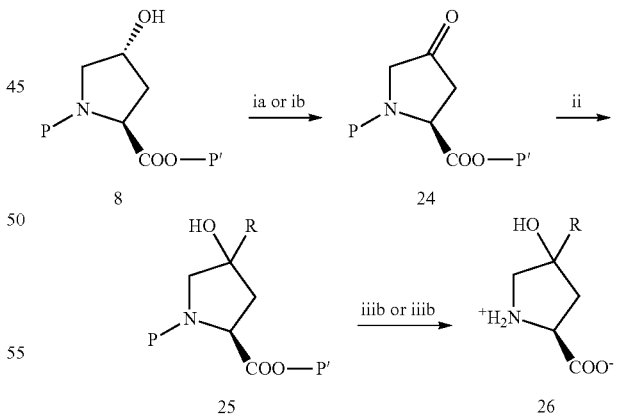

R = any alkyl or aryl group P = trityl or CBZ protected
P' = H or ethyl ester
(ia) CrO₃, H₂SO₄, Acetone or (ib) Swern oxidation; (ii) organometallic/CuBr or CuCN catalyst (2 eq.), Et₂O, -20° C.; (iiia) 10% Pd/C (.10% weight eq.), H₂, MeOH, H₂O, NH₄⁺ Acetate or (iiib) 1. KOH, THF; 2. HCl, THF.

Protected 4-hydroxy-proline 8, N-trityl and ethyl ester or N-Cbz, was converted to the 4-keto-proline 24 by either Swern oxidation or Jones oxidation respectively, in good yield 80-85% (Scheme 5; Bridges et al., "Conformationally defined neurotransmitter analogs. Selective inhibition of glutamate uptake by one pyrrolidine-2,4-dicarboxylate diastereomer," *J. Med. Chem.* 34(2):717-725 (1991)). Depending upon the protection group employed, triphenylmethyl (trityl) or Cbz, the stereochemistry of geminal addition via Grignard reagent to the 4-carbonyl was controlled. Geminal addition to a N-trityl protected 4-keto-proline was selective preferring the trans-alcohol product, whereas, addition to a N-Cbz protected 4-keto-proline was selective preferring the cis product, with no detectable trace of a contaminating diastereomer. The final protect 26 was obtained after deprotection under standard conditions and ion exchange. Briefly, trans-4-hydroxy-L-proline was protected via 1.) thionyl-chloride, EtOH; 2.) triphenylmethylchloride, triethylamine, $CH_2Cl_2$ at 22° C. to produce N-trityl-trans-4-hydroxy-L-proline ethyl ester or benzylchloroformate, NaOH, $H_2O$, 22° C. to produce N-Cbz-trans-4-hydroxy-L-proline. The protected 4-hydroxy proline was then oxidized to the 4-keto-proline via Swern oxidation (1. Oxalyl chloride, DMSO 2. TEA) (if trityl protecting group was present) or by Jones oxidation ($CrO_3$, $H_2SO_4$, Acetone) (if Cbz protecting group was present) and isolated by silica gel. The isolated protected 4-keto-proline was then transformed to the 4-alkyl-4-hydroxy proline via Cu(I) catalyzed ($R_2CuMgBr$) Grignard or organo lithium ($R_2CuLi$) addition at −20° C. in $Et_2O$. Importantly, it was necessary to isolate the product by silica gel with 1% triethylamine (TEA) immediately after the Grignard or organo lithium addition reaction when N-trityl-4-keto-proline was used as a starting material so as to avoid decomposition. Once isolated, the product was then deprotected under standard conditions using 1.2 eq. KOH in THF at 22° C. to hydrolyze the ethyl ester of N-trityl-4,4-alkyl-hydroxyproline followed by dilute HCl 1.2 eq. in THF at room temperature and isolated by washing with 1:1 EtOAc, $CH_2Cl_2$ and ion exchange. Alternatively, N-Cbz-4,4-alkyl-hydroxy-proline was deprotected by hydrogenolysis with 10% Pd/carbon (0.1 eq) at 22° C. in MeOH and isolated by washing with 1:1 EtOAc, $CH_2Cl_2$ and ion exchange. The final product dissolved in water/buffer from the ion exchange, regardless of the protection groups used, was then concentrated by lyophilization to a dry solid.

N-Trityl-4-keto-L-proline ethyl ester: BRL: 41

To a 100 mL round bottom flask containing 20 mL $CH_2Cl_2$ was added 0.54 mL (6.20 mmol; 1.2 eq) of $COCl_2$ in 2 mL $CH_2Cl_2$. The flask was then chilled to −60° C. (acetone bath and cold finger) under argon balloon. To this was added 0.88 mL dry (molecular civ treated) DMSO in 1 mL dry ($MgSO_4$ treated) $CH_2Cl_2$ drop wise. The mixture was allowed to stir for 15 min. before being brought up to −30° C. where 2.02 g (6.17 mmol) of N-trityl-trans-4-hydroxy-L-proline ethyl ester in 4 mL $CH_2Cl_2$ was added dropwise over 10 min. The resulting solution was allowed to stir for 1 h at −30° C. under argon balloon. To complete the reaction, 3.6 mL (>5 eq) of triethylamine was slowly added. The flask was then allowed to warm to room temperature where 100 mL of water was added. The mixture was then extracted with $Et_2O$ (3×100 mL). The organic extracts were combined, dried with $Na_2SO_4$ and concentrated via rotovap to a solid crude. The remaining crude was then immediately separated by silica gel (90% hexanes, 9% ethylacetate, 1% TEA, $R_f$=0.2). The fractions containing the product were combined, concentrated, and placed on a high vacuum pump leaving 1.51 g of N-trityl-4-keto-L-proline ethyl ester, as a white foam, a yield of 75%. This product, once isolated, was then used within 4-6 h in the addition step (trityl group readily decomposes) without further purification.

N-Trityl-cis-4-methyl-trans-4-hydroxy-L-proline ethyl ester: BRL: 70

To a flame dried/argon purged flask containing 0.123 g (5.00 mmol; 2 eq) of Mg metal in 2 mL diethyl ether was added 0.315 mL (5.00 mmol; 2 eq) of iodomethane over 10 min. The mixture was allowed to stir for approximately 20 min. until when it was observed that most or all of the Mg metal was consumed. The flask was cooled to −20° C. under argon balloon where it was then transferred to a flask containing 0.359 mg (2.5 mmol; 1 eq) of Cu(I)Br (dried by vacuum) at −20° C. The mixture was allowed to stir for approximately 15 min. after which 1.00 g (2.50 mmol) of N-trityl-4-keto-L-proline ethyl ester in 6 mL dry $Et_2O$ was added and allowed to stir overnight. The reaction was then quenched by the addition of 15 mL saturated $NH_4Cl$ solution, and diluted with 100 mL $Et_2O$. The organic phase was washed with water (3×100 mL), dried over $Na_2SO_4$ and concentrated via rotovap to a light brown foam. Immediately following the addition step the product, 0.624 g N-Trityl-cis-4-methyl-trans-4-hydroxy-L-proline ethyl ester, was isolated by a silica gel (95% hexanes, 4% ethyl acetate, 1% TEA; $R_f$=0.12), a yield of 60%.

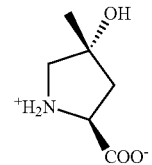

CSE95

Chemical Formula: $C_6H_{11}NO_3$
Molecular Weight: 145.16 cis-4-methyl-trans-4-hydroxy-L-proline: BRL: 71/CSE95

To 0.111 g (0.276 mmol) of N-Trityl-cis-4-methyl-trans-4-hydroxy-L-proline ethyl ester was added 2 mL of THF, 0.2 mL $H_2O$ and 20.0 mg (90%, 1.2 eq) KOH. The mixture was allowed to stir for 2 h at room temperature. The solution was then concentrated to a solid residue by rotovap, and washed with water (2×10 mL). The remaining residue was resuspended in 2 mL THF and 0.33 mL (2.5 eq) of 2 M HCl was added. After 1 h of stirring the solution was diluted with 10 mL water. The THF was removed by rotovap leaving mostly water and dissolved product. The sample was frozen and lyophilized to concentrate. The remaining residue was washed 1:1 EtOAc/$CH_2Cl_2$ (3×10 mL). The sample was then diluted with 5 mL water and isolated by cation exchange resin (sulphonic acid resin) using 10% $NH_4OAc$ to elute the final product, cis-4-methyl-trans-4-hydroxy-L-proline. The collected fractions were combined and concentrated by lyophilization to afford 32 mg of the product, an 83% yield. HRMS m/e calcd. For $C_6H_{12}NO_3$=146.0817. found 146.0803.

N-Cbz-4-keto-L-proline ethyl ester: BRL: 47

To a round bottom flask containing 14.0 g (52.8 mmol) of N-Cbz-4-hydroxy-L-proline 8 was added 26 mL acetone.

The solution was cooled on ice bath where 8.12 mL (0.106 mmol; 2 eq) of Jones reagent ($CrO_3$, $H_2SO_4$, 1.3 M in water) was added. The mixture was allowed to warm to room temperature and stir for 3 h where the reaction appeared to be complete, as determined by TLC. The reaction was quenched by the addition of 6 mL isopropanol. After stirring for another 2 h the flask was placed on a glass socket rotovap and the isopropanol/acetone was removed by reduced pressure. The remaining green residue was then diluted into 200 mL water, salted with NaCl and extracted with EtOAc (3×200 mL). The organic extracts were combined, dried with $MgSO_4$, filtered and concentrated to an oil. The remaining yellow oil was then separated by silica gel (90% $CH_2Cl_2$, 9% MeOH, 1% AcOH, $R_f$=0.3). The fractions containing the product were combined and concentrated by rotovap to a solid residue and then recrystallized from $CH_2Cl_2$ leaving 9.86 g (37.5 mmol) of N-Cbz-4-keto-L-proline, a 71% yield. The product material was used in the next synthetic step without further purification.

N-Cbz-trans-4-methyl-cis-4-hydroxy-L-proline: BRL: 53

To a flame dried/argon purged flask containing 0.231 g (9.40 mmol; 2.5 eq) Mg metal in 2 mL dry diethyl ether was added 0.530 mL (8.40 mmol; 2.2 eq) of iodomethane slowly. The mixture was allowed to stir for approximately 20 min. until when it was observed that most or all of the Mg metal was consumed. The mixture was then cooled to −20° C. under argon balloon. To this prepared Grignard was added 1.00 g (2.50 mmol) of N-Cbz-4-keto-L-proline in 5 mL cold dry $Et_2O$. The mixture was allowed to return to rt and then refluxed for 2 h. The reaction was then quenched by the addition of 15 mL saturated $NH_4Cl$ aq and allowed to stir an additional 30 min. The mixture was then acidified with HCl to approximately pH 2, salted with NaCl and extracted with EtOAc (3×100 mL). The organic extracts were then combined, dried with $MgSO_4$, filtered, and concentrated to a light brown residue. The product, 0.440 g (1.58 mmol) of N-Cbz-trans-4-methyl-cis-4-hydroxy-L-proline, was isolated by a silica gel (85% $CH_2Cl_2$, 14% MeOH, 1% AcOH; $R_f$=0.25) with a yield of 41%; not including full recovery of unreacted starting material. The isolated product was then used in the deprotection step without further purification.

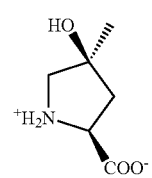

CSE96

Chemical Formula: $C_6H_{11}NO_3$
Molecular Weight: 145.16 cis-4-hydroxy-trans-4-methyl-L-proline: BRL: 56/CSE96

To 0.200 g (0.716 mmol) of N-Cbz-cis-4-hydroxy-trans-4-methyl-L-proline was added 2 2 mL MeOH which was transferred to a pressure flask containing 50 mg 10% Pd/carbon and 0.2 mL $H_2O$. This was then connected to a Parr shaker and the air was removed by vacuum. The container was filled with 50 psi $H_2$ (g) and the apparatus was allowed to shake overnight. The flask was then vented and the contents were diluted with 20 mL water and filtered through CM-cellulose. The filtrate was then frozen and concentrated by lyophilization to a light brown residue that was then washed with 1:1 $EtOAc:CH_2Cl_2$ (3×10 mL). The sample was then diluted with 5 mL water and isolated by cation exchange resin (sulphonic acid resin) using 10% ammonium acetate to elute the final product. The collected fractions were combined and concentrated by lyophilization to afford 62 mg of cis-4-hydroxy-trans-4-methyl-L-proline, a 60% yield. HRMS m/e calcd. For $C_6H_{12}NO_3$=146.0817. found 146.0823.

Example 7

ASCT Expression and Electrophysiological Recordings in *Xenopus lavies* Oocytes

Figure 4:
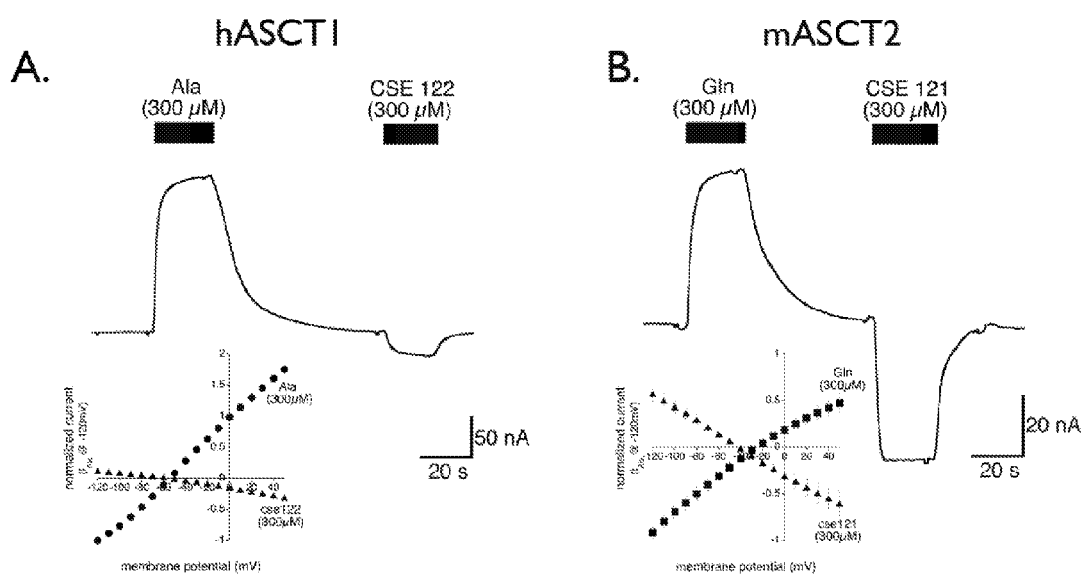
FIG. 4 shows hydroxy proline derivatives CSE 121 (300 µM) and CSE 122 (300 µM) blocking a leak current in mASCT2 and hASCT1, opposite the current induced by substrate (–20 mV). A. Inset: The current and voltage relationship for hASCT1 currents activated by alanine or blocked by CSE 122 resolved by subtracting away voltage jumps in Ringer solution. B. Inset: The current and voltage relationship for mASCT2 currents activated by glutamine or blocked by CSE 121 resolved by subtracting away voltage jumps in Ringer solution.

Human ASCT1 and murine ASCT2 cRNA were microinjected in stage V-VI oocytes. Uncoupled anion currents associated with the transport of substrate were recorded 3-5 days later as previously described (Zerangue & Kavanaugh, 1996). Recording solution contained 50 mM NaCl, 50 mM NaSCN, 2 mM KCl, 1 mM $MgCl_2$, 1.8 mM $CaCl_2$, and 5 mM HEPES (pH 7.4). Using two-electrode voltage clamp (TEVC), oocytes were held at −20 mV. Microelectrodes were filled with 3M KCl and had resistances from 1 to 3 MΩ. Recordings were performed at 22° C. with a Geneclamp 500 amplifier connected to a PowerLab 2/26 (AD instruments). The digital output was interfaced to a MacBook Pro (Macintosh) using Chart v7.1.2 software. The currents were low-pass filtered at 10 Hz and acquired at 20 Hz. Data was analyzed offline and modeling and fitting of substrate concentration-dependence of the currents was performed with Kaleidagraph software (v 4.04). The concentration dependent percent block of the anion leak or substrate activation of the anion current were fit with the Michaelis-Menten equation ($I_{anion}=I_{max}\times[Drug]/(K_m+[Drug])$) to define the $K_i$ of inhibition or the apparent affinity ($K_m$) of transport, respectively. FIG. 4 shows examples of currents induced by substrates and blocked by inhibitors. Table 1 shows $K_i$ estimates or actual $K_i$ (*) derived from inhibition of an anion leak current by the compounds of the invention (i.e., CSE compounds) in *Xenopus* oocytes expressing human ASCT1 or mouse ASCT2. The lower the number the more active or potent the prolinol is towards inhibiting the ASC transporters.

TABLE 1

| CSE # | Chemical Structure | Ki (μM) ACST1 | Ki (μM) ASCT2 |
|---|---|---|---|
| CSE95 | 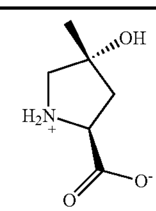 | >500 | 926 +/−252 |
| CSE96 | 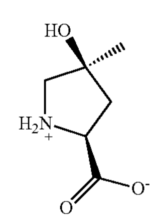 | >500 | 1077 +/−322 |

TABLE 1-continued

| CSE # | Chemical Structure | Ki (μM) ACST1 | Ki (μM) ASCT2 |
|---|---|---|---|
| CSE103 | 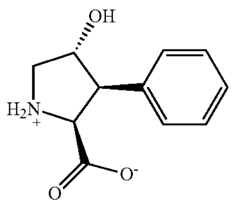 [SMILES: O=C([O-])[C@H]1[NH2+]C[C@H](O)[C@H]1c1ccccc1] | 332 +/−74 | 1128 +/−318 |
| CSE104 | 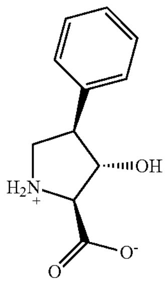 | >500 | >500 |
| CSE109 | 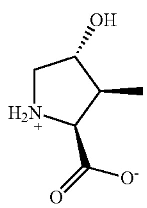 | 564 +/−149 | 922 +/−316 |
| CSE110 | 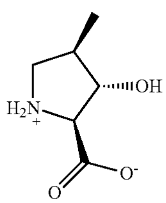 | 1050 +/−110 | 1149 +/−283 |
| CSE111 | 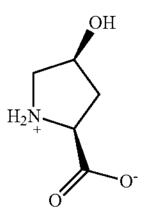 | 805 +/−148 | 872 +/−201 |
| CSE113 | 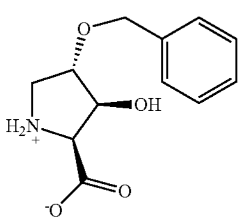 | 493 +/−61 | 828 +/−248 |
| CSE115 | 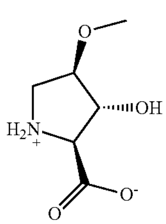 | 214* +/−32 | 235* +/−69 |
| CSE117 | | 594 +/−191 | 502 +/−110 |
| CSE118 | | 150 +/−43 | 141* +/−20 |
| CSE121 | | 39* +/−5 | 69* +/−7 |
| CSE122 | | 237* +/−40 | 268* +/−70 |
| CSE124 | | 481 +/−77 | 600 +/−176 |
| CSE127 | | >500 | >500 |

TABLE 1-continued

| CSE # | Chemical Structure | Ki (μM) ACST1 | Ki (μM) ASCT2 |
|---|---|---|---|
| CSE130 | 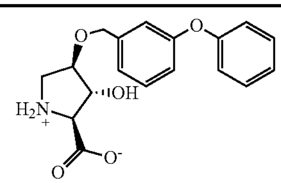 | 13* +/−2 | 10* +/−2 |
| CSE131 | 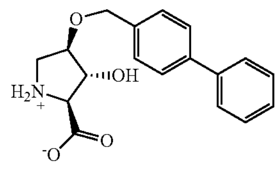 | 0.31* +/−0.04 | 0.24* +/−0.04 |
| CSE132 | 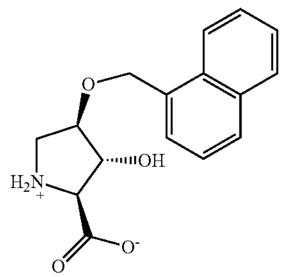 [SMILES: O=C([O-])[C@H]1[NH2+]C[C@@H](OCc2cccc3ccccc23)[C@@H]1O] | ~10 | ~10 |

Example 8

Radlolabeled Uptake in *Xenopus laevis* Oocytes

Briefly, uptake in oocytes was measured 3-5 days following microinjection of 50 ng of hASCT1 or mASCT2 cRNA as described (Zerangue and Kavanaugh, "ASCT-1 is a Neutral Amino Acid Exchanger with Chloride Channel Activity," *J. Bio. Chem.* 271(45):27991-27994 (1996), herein incorporated by reference in its entirety). Uptake was measured following 10 minute incubation in [$^3$H]L-alanine or [$^3$H]L-glutamine, respectively (10 μM; 1 μCi/mL in ND96 Ringer pH 7.4). Assays were performed in the presence or absence of varying concentrations of test compounds. After 10 min., oocytes were lysed by addition of 2 M NaOH (1 mL) and placed in vials for quantification by scintillation spectroscopy. Homo- or hetero-exchange of intracellular L-[$^3$H]-alanine preloaded into oocytes expressing hASCT1 or mASCT2 over a course of 20 minutes was measured by quantifying radioactivity release induced by 1 mM of substrates (L-glutamine, or L-alanine) or 1 mM trans-3-hydroxy-L-proline or other test compounds in 2 mL ND96 buffer. 10 μL samples were taken at 1 min. intervals and placed into scintillation vial for quantification.

Example 9

Use of the Subject Compounds as Research Tools

The compounds of the subject invention can be used as pharmacologic tools to study effects, including, but not limited to, the inhibition of amino acid transport. For example, the compounds of the invention can be used to delineate the function and physiological significance of the excitatory amino acid transporters (EAATs) or to investigate the function and significance of the System A transporters such as ATA1, ATA2, and SAT2. The compounds of the invention can be used experimentally in in vitro or in vivo studies.

In one example of the compounds of the invention being used as research tools, primary cortical cell cultures are prepared from E18 Sprague-Dawley rat embryos a cultured for 7 days as described by Berghuis et al. (*J. Neurobiol.* 66:1437-1451 (2006)). Subsequently, n=3 cultures (24-well inserts with 200,000 cells/insert) per condition are exposed to a compound of the invention with or without additional experimental compounds not the subject of the present invention. In parallel, identical cultures are treated as above with KCl (20 mM) as culture additive to evoke sustained depolarization of cortical neurons. After incubation, culture media (400 μL) is collected and snap-frozen for high-performance liquid chromatography (HPLC) analysis. In addition, cells are scraped into 0.05 M perchloric acid (100 μL per sample), lysed at 4° C. for 60 min., and stored at −80° C. until analysis to determine intracellular amino acid concentrations after neutralization with 0.05 M NaOH. Intracellular and extracellular amino acid concentrations are determined after pre-column derivatization by isocratic HPLC analysis of ortho-phtalaldehyde derivatives of glutamate, aspartate, and glutamine. Statistical analysis is performed by first testing differences between particular experimental groups (Student's t-test) followed by multivariate ANOVA design with [Gln], [KCl], and incubation time used as fixed variables.

In another example of the compounds of the invention being used as research tools, monkey kidney fibroblasts (CV-1 cells) are plated on collagen-coated 12-well dishes (2E5 cells/well) in DMEM containing 10% FBS, penicillin (100 units/mL), streptomycin (100 mg/mL), and glutamine (4 mM). Cells are rinsed with DMEM without serum, antibiotics, or glutamine, infected with recombinant virus (e.g., a vaccinia, adeno-, or lentivirus encoding an experimental protein not the subject of the present invention) at 10 plaque-forming units/cell for 30 min., and then transfecting with plasmid containing, e.g., SAT2 cDNA in CDM7/amp (1 ug/mL) by lipofection in the same medium. After 16 h, the cells are rinsed with uptake buffer containing 125 mM NaCl, 4.8 mM KCl, 1.2 mM $KH_2PO_4$, 1.2 mM $MgSO_4$, 1.2 mM $CaCl_2$, 5.6 mM glucose, and 25 mM HEPES, pH 7.4, and preincubated in the same buffer for 5 min. at 37° C. The medium is removed and replaced with fresh buffer at the indicated pH values to which various concentrations of unlabelled alanine of glutamine and 2.5 μCi of [$^3$H]alanine or [$^3$H]glutamine or 0.25 μCi (10 uM) of a [$^{14}$C]-labeled compound of the invention is added. For inhibition studies, 1.5 mM unlabeled amino acids are mixed with a [$^{14}$C]-labeled compound of the invention. Cells are placed in a 37° C. incubator for 2.5 min., and uptake is terminated with a 2.5 mL wash in 4° C. buffer on ice. For Na$^+$-free media, NaCl is replaced with equimolar $NaNO_2$ or sodium gluconate. Cells are then solubilized in 1 mL of 1% SDS, and radioactivity measured by scintillation counting in 5 mL of EcoScint (National Diagnostics). Transport measurements are performed in duplicate and repeated at least three times using independent infection/transfections. All experimental conditions with, e.g., SAT2-transfected cells, have corresponding mock-transfected cells in adjacent wells.

Example 10

Additional Compounds of the Invention

The aryl or aryl-ether-trans-hydroxy-L-proline analog compounds of the invention can be optimized to alter the potency or selectivity of ASCT2 or ASCT1 inhibition. One means of optimization includes, but is not limited to, the addition of X=halogens (Chlorine, Fluorine, Bromine), methyl, methoxy, isopropyl, phenyl or trifluoromethyl groups to the aryl rings of the synthesized analogs, multiple additions, or altered regiochemistry. The compound structures featured in Table 2 illustrate such analog optimization encompassed by the present invention.

TABLE 2

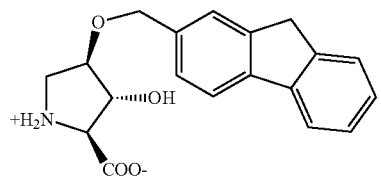

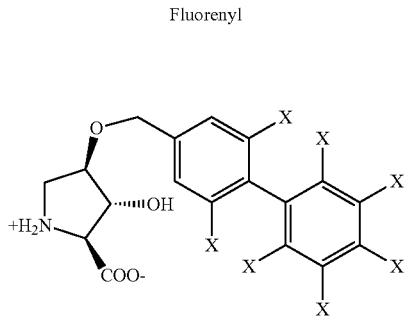

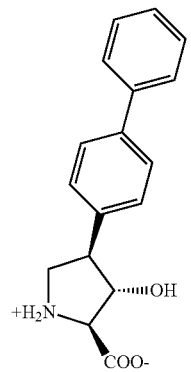

TABLE 2-continued

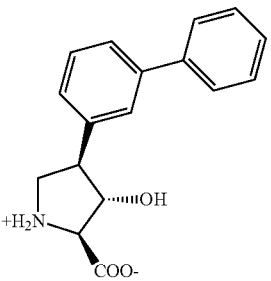

Fluorenyl

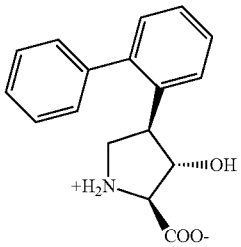

Multiple additions

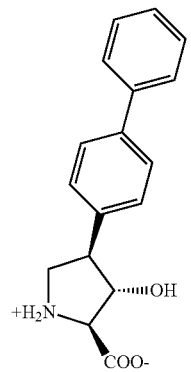

Variable regiochemistry

TABLE 2-continued

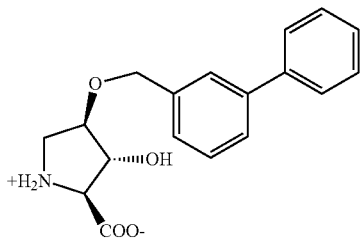

Example 11

Additional Compounds of the Invention

Figure 5:
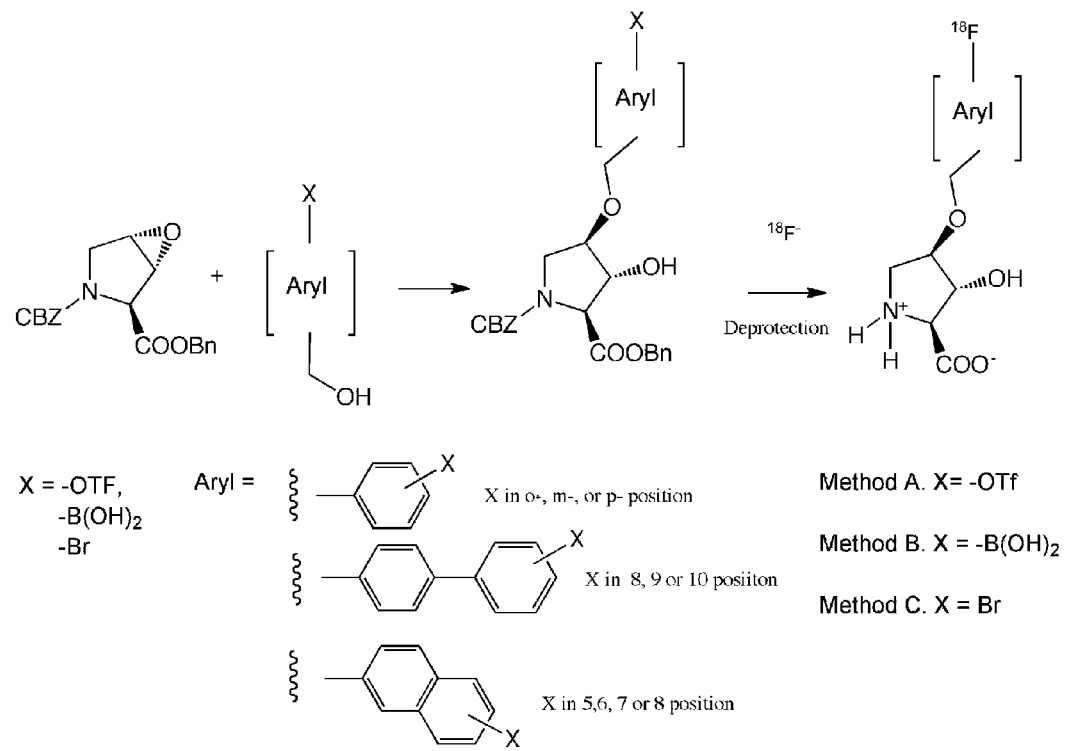
FIG. 5 shows three exemplary chemical synthetic pathways to produce a radiolabeled compound of the invention. In this case, the methods A, B, C may be used to produce fluorine-18-CSE-131.

Various methods can be used to allow for the facile and direct incorporation of radiolabeled fluorine into compounds of the invention, including compounds with complex functional groups. Such compounds are useful as diagnostic agents in, e.g., positron emission tomography (PET). Three different methods of radiofluorinating an exemplary compound of the invention, CSE-13, for use as positron emission tomography (PET) agent, are shown in FIG. 5.

Method A, which uses the readily available Aryl triflates and CsF as the fluorinating agent, was the first palladium catalyzed method which proceeds in high conversion and relatively short reaction times, necessary for the use of $^{18}$F with a half-life of 110 minutes. Some complications are observed with proto-detriflylation, and in some cases mixtures of regioisomers were observed (the later is not a major issue for CSE-131).

Method B begins with aryl boronates, which are reacted to form stable palladium complexes, and the reaction time with a second electrophilic fluoride palladium complex takes place in high radiochemical yield (RCY) in acetone at 85° C. in 10 minutes.

In Method C, the $Ni^{2+}$/oxidant method uses an aqueous $^{18}$F solution, and as such eliminates the need for time-consuming anion-exchange and azeotropic drying steps during the synthesis of the diagnostic PET compound. Radiofluorination takes place selectively in the presence of normally sensitive functional groups such as ester and protected nitrogen, proceeds at room temperature and is complete within less than one minute. The Nickel complexes are isolable and stable, and prepared from the bromides.

The synthetic schemes described in methods A, B, and C can be used by a skilled artisan to generate additional compounds of the invention. For example, these schemes can be used to arrive at a radiolabeled CSE-117 as shown by the following chemical structure, where X represents a halogen or radionuclide (e.g., $^{18}$F) at the ortho, meta, or para position of the aromatic ring:

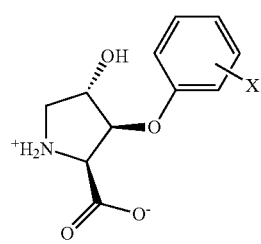

All Embodiments

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

Other embodiments are within the claims.

What is claimed is:

1. A compound represented by Formula I or II:

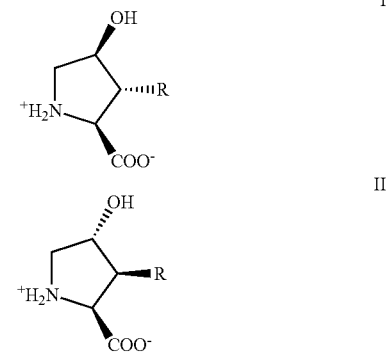

or a salt or ester thereof, wherein

R is selected from the group consisting of a halogen, a radionuclide, an alkyl-ether, an aryl, and an aryl-ether, wherein said aryl is not a phenyl, and wherein said alkyl-ether, aryl, or aryl-ether further comprises a halogen or radionuclide.

2. The compound of claim 1, wherein said halogen is fluorine.

3. The compound of claim 1, wherein said halogen or radionuclide is fluorine-18.

4. The compound of claim 1, wherein said radionuclide is selected from the group consisting of carbon-11, nitrogen-13, oxygen-15, fluorine-18, zinc-62, copper-62, gallium-68, germanium-68, strontium-82, technicium-94m, iodine 124, or rubidium-82.

5. The compound of claim 3, wherein said fluorine-18 has a specific activity of at least 1.0 Ci/mmol.

6. The compound of claim 3, wherein said fluorine-18 has a specific activity of at least 2.0 Ci/mmol.

7. The compound of claim 1 in combination with a pharmaceutically acceptable excipient.

8. The compound of claim 1 selected from the group consisting of trans-3-benzyloxy-cis-4-hydroxy-L-proline, (2S,3S,4S)-3-phenoxy-4-hydroxy-proline, cis-4-hydroxy-trans-3-methoxy-L-proline, and cis-4-hydroxy-trans-3-isopropoxy-L-proline.

* * * * *